(12) United States Patent
Hohjoh et al.

(10) Patent No.: US 8,946,185 B2
(45) Date of Patent: Feb. 3, 2015

(54) AGENT FOR SUPPRESSING EXPRESSION OF DOMINANT ALLELE

(75) Inventors: Hirohiko Hohjoh, Tokyo (JP); Masaki Takahashi, Tokyo (JP)

(73) Assignee: LSIP, LLC, Tokyo (JP)

( * ) Notice: Subject to any disclaimer, the term of this patent is extended or adjusted under 35 U.S.C. 154(b) by 12 days.

(21) Appl. No.: 13/805,063

(22) PCT Filed: Jun. 17, 2011

(86) PCT No.: PCT/JP2011/063878
§ 371 (c)(1),
(2), (4) Date: Dec. 18, 2012

(87) PCT Pub. No.: WO2011/158924
PCT Pub. Date: Dec. 22, 2011

(65) Prior Publication Data
US 2013/0090373 A1    Apr. 11, 2013

(30) Foreign Application Priority Data

Jun. 18, 2010  (JP) ................. 2010-139925

(51) Int. Cl.
*C12N 15/11*  (2006.01)
*C12Q 1/68*  (2006.01)
*C12N 15/113*  (2010.01)
*A61K 31/713*  (2006.01)

(52) U.S. Cl.
CPC ............ *C12N 15/113* (2013.01); *A61K 31/713* (2013.01); *C12N 15/111* (2013.01); *C12N 2310/14* (2013.01); *C12N 2310/533* (2013.01); *C12N 2320/34* (2013.01)
USPC ......................................... 514/44 A; 435/6.1

(58) Field of Classification Search
None
See application file for complete search history.

(56) References Cited

U.S. PATENT DOCUMENTS

2007/0259827 A1* 11/2007 Aronin et al. ................... 514/44
2009/0253132 A1* 10/2009 Kaplan et al. ...................... 435/6

FOREIGN PATENT DOCUMENTS

JP        2011-125219        6/2011

OTHER PUBLICATIONS

Ohnishi et al, Enhancement of Allele Discrimination by Introduction of Nucleotide Mismatches into siRNA in Allele-Specific Gene Silencing by RNAi, 2008, PLoS ONE 3(5): 1-9.*

Ohnishi, Yusuke, et al., "Enhancement of Allele Discrimination by Introduction of Nucleotide Mismatches Into siRNA in Allele-Specific Gene Silencing by RNAi", PLoS ONE, vol. 3, Issue 5, May 2008, e2248, pp. 1-9.
Inukai, Michio, et al., "Presence of Epidermal Growth Factor Receptor Gene T790M Mutation As a Minor Clone in Non-Small Cell Lung Cancer", Cancer Research, vol. 66, Aug. 15, 2006, pp. 7854-7858.
Furuya, Hirokazu, et al., "A Unique Case of Fibrodysplasia Ossificans Progressiva With an ACVR1 Mutation, G356D, Other Than the Common Mutation (R206H)", American Journal of Medical Genetics, vol. 146A, 2008, pp. 459-463.
Pfister, Edith L., et al., "Five siRNAs Targeting Three SNPs in Huntingtin May Provide Therapy for Three-Quarters of Huntington's Disease Patients", Current Biology, vol. 19, 2009, pp. 774-778.
Yusuke Onishi, "Kairyogata siRNA Ni Yoru Allyl Tokuiteki Idenshi Hatsugen Yokusei" Igaku no Ayumi, vol. 227, No. 11, 2008, pp. 1007-1008 with English Abstract.
Takahashi, Masaki, et al., "Tailor-Made RNAi Knockdown Against Triplet Repeat Disease-Causing Alleles", Proceedings of the National Academy of Sciences of the United States of America, vol. 107, No. 50, Dec. 14, 2010, pp. 21731-21736.
Geng, Chang-ming, et al., "Double-Mismatched siRNAs Enhance Selective Gene Silencing of a Mutant ALS-Causing Allele", Acta Pharmacol Sin, vol. 29, 2008, pp. 211-216.
Scholefield, Janine, et al., Design of RNAi Hairpins for Mutation-Specific Silencing of Ataxin-7 and Correction of a SCA7 Phenotype, PLOS ONE, vol. 4, No. 9, p. e7232, Sep. 2009.
Miller, Victor M., et al., Allele-specific silencing of dominant disease genes, PNAS, vol. 100, No. 12, pp. 7195-7200, Jun. 10, 2003.
Feng, Xiaorong, et al., Allele-specific silencing of Alzheimer's disease genes the amyloid precursor protein genes with Swedish or London mutations, Gene, vol. 371, No. 1, pp. 68-74, 2006.
Teng, Xu, et al., Differential inhibition of lamivudine-resistant hepatitis B virus by allele-specific RNAi, Journal of Virological Methods, vol. 168, No. 1-2, pp. 6-12, 2010.
Takahashi, M., et al., Disease-causing allele-specific silencing against the ALK2 mutants, R206H and G356D, in fibrodysplasia ossificans progressiva, Gene Therapy, vol. 19, No. 7, pp. 781-785, Dec. 2011.
Supplementary European Search Report issued in corresponding European Application No. 11795826, Oct. 27, 2014, 2 pages.

\* cited by examiner

*Primary Examiner* — Tracy Vivlemore
*Assistant Examiner* — Kate Poliakova
(74) *Attorney, Agent, or Firm* — Edwards Wildman Palmer LLP; David G. Conlin; George W. Neuner

(57) ABSTRACT

An agent for selectively suppressing the expression of a dominant allele while allowing expression of wild-type or desired alleles and methods for using the agent are described. The RNAi agent has a structure obtained by assigning a dominant point mutation in the targeted allele as a standard point, setting a base length from the standard point to the 5' end to a predetermined length, and introducing one mismatch base differing from the target sequence to a predetermined position downstream from the standard point.

9 Claims, 8 Drawing Sheets

A

B

```
                        SEQUENCE LISTING

<160> NUMBER OF SEQ ID NOS: 92

<210> SEQ ID NO 1
<211> LENGTH: 19
<212> TYPE: RNA
<213> ORGANISM: Artificial
<220> FEATURE:
<223> OTHER INFORMATION: human ALK2 siRNA

<400> SEQUENCE: 1
aguggcucac cagauuaca                                                    19

<210> SEQ ID NO 2
<211> LENGTH: 19
<212> TYPE: RNA
<213> ORGANISM: Artificial
<220> FEATURE:
<223> OTHER INFORMATION: human ALK2 siRNA

<400> SEQUENCE: 2
uguaaucugg ugagccacu                                                    19

<210> SEQ ID NO 3
<211> LENGTH: 19
<212> TYPE: RNA
<213> ORGANISM: Artificial
<220> FEATURE:
<223> OTHER INFORMATION: human ALK2 siRNA

<400> SEQUENCE: 3
aguggcucac cacauuaca                                                    19

<210> SEQ ID NO 4
<211> LENGTH: 19
<212> TYPE: RNA
<213> ORGANISM: Artificial
<220> FEATURE:
<223> OTHER INFORMATION: human ALK2 siRNA

<400> SEQUENCE: 4
uguaaugugg ugagccacu                                                    19

<210> SEQ ID NO 5
<211> LENGTH: 19
<212> TYPE: RNA
<213> ORGANISM: Artificial
<220> FEATURE:
<223> OTHER INFORMATION: human ALK2 siRNA

<400> SEQUENCE: 5
aguggcucac caguuuaca                                                    19

<210> SEQ ID NO 6
<211> LENGTH: 19
<212> TYPE: RNA
<213> ORGANISM: Artificial
<220> FEATURE:
```

```
<223> OTHER INFORMATION: human ALK2 siRNA

<400> SEQUENCE: 6
uguaaacugg ugagccacu                                                19

<210> SEQ ID NO 7
<211> LENGTH: 19
<212> TYPE: RNA
<213> ORGANISM: Artificial
<220> FEATURE:
<223> OTHER INFORMATION: human ALK2 siRNA

<400> SEQUENCE: 7
aguggcucac cagguuaca                                                19

<210> SEQ ID NO 8
<211> LENGTH: 19
<212> TYPE: RNA
<213> ORGANISM: Artificial
<220> FEATURE:
<223> OTHER INFORMATION: human ALK2 siRNA

<400> SEQUENCE: 8
uguaaccugg ugagccacu                                                19

<210> SEQ ID NO 9
<211> LENGTH: 19
<212> TYPE: RNA
<213> ORGANISM: Artificial
<220> FEATURE:
<223> OTHER INFORMATION: human ALK2 siRNA

<400> SEQUENCE: 9
aguggcucac cagcuuaca                                                19

<210> SEQ ID NO 10
<211> LENGTH: 19
<212> TYPE: RNA
<213> ORGANISM: Artificial
<220> FEATURE:
<223> OTHER INFORMATION: human ALK2 siRNA

<400> SEQUENCE: 10
uguaagcugg ugagccacu                                                19

<210> SEQ ID NO 11
<211> LENGTH: 18
<212> TYPE: RNA
<213> ORGANISM: Artificial
<220> FEATURE:
<223> OTHER INFORMATION: human ALK2 siRNA

<400> SEQUENCE: 11
guggcucacc aguuuaca                                                 18

<210> SEQ ID NO 12
<211> LENGTH: 18
<212> TYPE: RNA
<213> ORGANISM: Artificial
<220> FEATURE:
<223> OTHER INFORMATION: human ALK2 siRNA

<400> SEQUENCE: 12
uguaaacugg ugagccac                                                 18
```

```
<210> SEQ ID NO 13
<211> LENGTH: 19
<212> TYPE: RNA
<213> ORGANISM: Artificial
<220> FEATURE:
<223> OTHER INFORMATION: human ALK2 siRNA

<400> SEQUENCE: 13
guggcucacc aguuuacac                                              19

<210> SEQ ID NO 14
<211> LENGTH: 19
<212> TYPE: RNA
<213> ORGANISM: Artificial
<220> FEATURE:
<223> OTHER INFORMATION: human ALK2 siRNA

<400> SEQUENCE: 14
guguaaacug gugagccac                                              19

<210> SEQ ID NO 15
<211> LENGTH: 19
<212> TYPE: RNA
<213> ORGANISM: Artificial
<220> FEATURE:
<223> OTHER INFORMATION: human ALK2 siRNA

<400> SEQUENCE: 15
cagauuugga ccuggcagu                                              19

<210> SEQ ID NO 16
<211> LENGTH: 19
<212> TYPE: RNA
<213> ORGANISM: Artificial
<220> FEATURE:
<223> OTHER INFORMATION: human ALK2 siRNA

<400> SEQUENCE: 16
acugccaggu ccaaaucug                                              19

<210> SEQ ID NO 17
<211> LENGTH: 19
<212> TYPE: RNA
<213> ORGANISM: Artificial
<220> FEATURE:
<223> OTHER INFORMATION: human ALK2 siRNA

<400> SEQUENCE: 17
cagauuugga cguggcagu                                              19

<210> SEQ ID NO 18
<211> LENGTH: 19
<212> TYPE: RNA
<213> ORGANISM: Artificial
<220> FEATURE:
<223> OTHER INFORMATION: human ALK2 siRNA

<400> SEQUENCE: 18
acugccacgu ccaaaucug                                              19

<210> SEQ ID NO 19
<211> LENGTH: 19
<212> TYPE: RNA
<213> ORGANISM: Artificial
<220> FEATURE:
<223> OTHER INFORMATION: human ALK2 siRNA
```

```
<400> SEQUENCE: 19
cagauuugga ccaggcagu                                                   19

<210> SEQ ID NO 20
<211> LENGTH: 19
<212> TYPE: RNA
<213> ORGANISM: Artificial
<220> FEATURE:
<223> OTHER INFORMATION: human ALK2 siRNA

<400> SEQUENCE: 20
acugccuggu ccaaaucug                                                   19

<210> SEQ ID NO 21
<211> LENGTH: 19
<212> TYPE: RNA
<213> ORGANISM: Artificial
<220> FEATURE:
<223> OTHER INFORMATION: human ALK2 siRNA

<400> SEQUENCE: 21
cagauuugga ccucgcagu                                                   19

<210> SEQ ID NO 22
<211> LENGTH: 19
<212> TYPE: RNA
<213> ORGANISM: Artificial
<220> FEATURE:
<223> OTHER INFORMATION: human ALK2 siRNA

<400> SEQUENCE: 22
acugcgaggu ccaaaucug                                                   19

<210> SEQ ID NO 23
<211> LENGTH: 19
<212> TYPE: RNA
<213> ORGANISM: Artificial
<220> FEATURE:
<223> OTHER INFORMATION: human ALK2 siRNA

<400> SEQUENCE: 23
cagauuugga ccugccagu                                                   19

<210> SEQ ID NO 24
<211> LENGTH: 19
<212> TYPE: RNA
<213> ORGANISM: Artificial
<220> FEATURE:
<223> OTHER INFORMATION: human ALK2 siRNA

<400> SEQUENCE: 24
acuggcaggu ccaaaucug                                                   19

<210> SEQ ID NO 25
<211> LENGTH: 19
<212> TYPE: RNA
<213> ORGANISM: Artificial
<220> FEATURE:
<223> OTHER INFORMATION: human ALK2 siRNA

<400> SEQUENCE: 25
cagauuugga ccugggagu                                                   19

<210> SEQ ID NO 26
<211> LENGTH: 19
```

<212> TYPE: RNA
<213> ORGANISM: Artificial
<220> FEATURE:
<223> OTHER INFORMATION: human ALK2 siRNA

<400> SEQUENCE: 26
acucccaggu ccaaaucug                                                        19

<210> SEQ ID NO 27
<211> LENGTH: 19
<212> TYPE: RNA
<213> ORGANISM: Artificial
<220> FEATURE:
<223> OTHER INFORMATION: human ALK2 siRNA

<400> SEQUENCE: 27
cagauuugga ccuggcugu                                                        19

<210> SEQ ID NO 28
<211> LENGTH: 19
<212> TYPE: RNA
<213> ORGANISM: Artificial
<220> FEATURE:
<223> OTHER INFORMATION: human ALK2 siRNA

<400> SEQUENCE: 28
acagccaggu ccaaaucug                                                        19

<210> SEQ ID NO 29
<211> LENGTH: 19
<212> TYPE: RNA
<213> ORGANISM: Artificial
<220> FEATURE:
<223> OTHER INFORMATION: human ALK2 siRNA

<400> SEQUENCE: 29
cagauuugga ccuggcacu                                                        19

<210> SEQ ID NO 30
<211> LENGTH: 19
<212> TYPE: RNA
<213> ORGANISM: Artificial
<220> FEATURE:
<223> OTHER INFORMATION: human ALK2 siRNA

<400> SEQUENCE: 30
agugccaggu ccaaaucug                                                        19

<210> SEQ ID NO 31
<211> LENGTH: 19
<212> TYPE: RNA
<213> ORGANISM: Artificial
<220> FEATURE:
<223> OTHER INFORMATION: human ALK2 siRNA

<400> SEQUENCE: 31
cagauuugga ccuggcaga                                                        19

<210> SEQ ID NO 32
<211> LENGTH: 19
<212> TYPE: RNA
<213> ORGANISM: Artificial
<220> FEATURE:
<223> OTHER INFORMATION: human ALK2 siRNA

<400> SEQUENCE: 32
ucugccaggu ccaaaucug                                                  19

<210> SEQ ID NO 33
<211> LENGTH: 19
<212> TYPE: RNA
<213> ORGANISM: Artificial
<220> FEATURE:
<223> OTHER INFORMATION: human ALK2 siRNA

<400> SEQUENCE: 33
gcagauuugg accuggcag                                                  19

<210> SEQ ID NO 34
<211> LENGTH: 19
<212> TYPE: RNA
<213> ORGANISM: Artificial
<220> FEATURE:
<223> OTHER INFORMATION: human ALK2 siRNA

<400> SEQUENCE: 34
cugccagguc caaaucugc                                                  19

<210> SEQ ID NO 35
<211> LENGTH: 19
<212> TYPE: RNA
<213> ORGANISM: Artificial
<220> FEATURE:
<223> OTHER INFORMATION: human ALK2 siRNA

<400> SEQUENCE: 35
gcagauuugg accaggcag                                                  19

<210> SEQ ID NO 36
<211> LENGTH: 19
<212> TYPE: RNA
<213> ORGANISM: Artificial
<220> FEATURE:
<223> OTHER INFORMATION: human ALK2 siRNA

<400> SEQUENCE: 36
cugccugguc caaaucugc                                                  19

<210> SEQ ID NO 37
<211> LENGTH: 19
<212> TYPE: RNA
<213> ORGANISM: Artificial
<220> FEATURE:
<223> OTHER INFORMATION: human ALK2 siRNA

<400> SEQUENCE: 37
gcagauuugg accucgcag                                                  19

<210> SEQ ID NO 38
<211> LENGTH: 19
<212> TYPE: RNA
<213> ORGANISM: Artificial
<220> FEATURE:
<223> OTHER INFORMATION: human ALK2 siRNA

<400> SEQUENCE: 38
cugcgagguc caaaucugc                                                  19

<210> SEQ ID NO 39
<211> LENGTH: 19
<212> TYPE: RNA
<213> ORGANISM: Artificial

```
<220> FEATURE:
<223> OTHER INFORMATION: human ALK2 siRNA

<400> SEQUENCE: 39
gcagauuugg accugccag                                                    19

<210> SEQ ID NO 40
<211> LENGTH: 19
<212> TYPE: RNA
<213> ORGANISM: Artificial
<220> FEATURE:
<223> OTHER INFORMATION: human ALK2 siRNA

<400> SEQUENCE: 40
cuggcagguc caaaucugc                                                    19

<210> SEQ ID NO 41
<211> LENGTH: 19
<212> TYPE: RNA
<213> ORGANISM: Artificial
<220> FEATURE:
<223> OTHER INFORMATION: human ALK2 siRNA

<400> SEQUENCE: 41
gcagauuugg accugggag                                                    19

<210> SEQ ID NO 42
<211> LENGTH: 19
<212> TYPE: RNA
<213> ORGANISM: Artificial
<220> FEATURE:
<223> OTHER INFORMATION: human ALK2 siRNA

<400> SEQUENCE: 42
cucccagguc caaaucugc                                                    19

<210> SEQ ID NO 43
<211> LENGTH: 19
<212> TYPE: RNA
<213> ORGANISM: Artificial
<220> FEATURE:
<223> OTHER INFORMATION: human ALK2 siRNA

<400> SEQUENCE: 43
gcagauuugg accuggcug                                                    19

<210> SEQ ID NO 44
<211> LENGTH: 19
<212> TYPE: RNA
<213> ORGANISM: Artificial
<220> FEATURE:
<223> OTHER INFORMATION: human ALK2 siRNA

<400> SEQUENCE: 44
cagccagguc caaaucugc                                                    19

<210> SEQ ID NO 45
<211> LENGTH: 39
<212> TYPE: DNA
<213> ORGANISM: Homo sapiens
<220> FEATURE:
<223> OTHER INFORMATION: human ALK2 fragment

<400> SEQUENCE: 45
ctagcatgca agaacagtgg ctcaccagat tacactgta                              39
```

<210> SEQ ID NO 46
<211> LENGTH: 39
<212> TYPE: DNA
<213> ORGANISM: Homo sapiens
<220> FEATURE:
<223> OTHER INFORMATION: human ALK2 fragment

<400> SEQUENCE: 46
ggcctacagt gtaatctggt gagccactgt tcttgcatg                              39

<210> SEQ ID NO 47
<211> LENGTH: 39
<212> TYPE: DNA
<213> ORGANISM: Homo sapiens
<220> FEATURE:
<223> OTHER INFORMATION: human ALK2 fragment

<400> SEQUENCE: 47
ctagcatgca agaacagtgg ctcgccagat tacactgta                              39

<210> SEQ ID NO 48
<211> LENGTH: 39
<212> TYPE: DNA
<213> ORGANISM: Homo sapiens
<220> FEATURE:
<223> OTHER INFORMATION: human ALK2 fragment

<400> SEQUENCE: 48
ggcctacagt gtaatctggc gagccactgt tcttgcatg                              39

<210> SEQ ID NO 49
<211> LENGTH: 39
<212> TYPE: DNA
<213> ORGANISM: Homo sapiens
<220> FEATURE:
<223> OTHER INFORMATION: human ALK2 fragment

<400> SEQUENCE: 49
ctagcatgcg catagcagat ttggacctgg cagtcatga                              39

<210> SEQ ID NO 50
<211> LENGTH: 39
<212> TYPE: DNA
<213> ORGANISM: Homo sapiens
<220> FEATURE:
<223> OTHER INFORMATION: human ALK2 fragment

<400> SEQUENCE: 50
ggcctcatga ctgccaggtc caaatctgct atgcgcatg                              39

<210> SEQ ID NO 51
<211> LENGTH: 39
<212> TYPE: DNA
<213> ORGANISM: Homo sapiens
<220> FEATURE:
<223> OTHER INFORMATION: human ALK2 fragment

<400> SEQUENCE: 51
ctagcatgcg catagcagat ttgggcctgg cagtcatga                              39

<210> SEQ ID NO 52
<211> LENGTH: 39
<212> TYPE: DNA
<213> ORGANISM: Homo sapiens
<220> FEATURE:
<223> OTHER INFORMATION: human ALK2 fragment

```
<400> SEQUENCE: 52
ggcctcatga ctgccaggcc caaatctgct atgcgcatg                             39

<210> SEQ ID NO 53
<211> LENGTH: 19
<212> TYPE: RNA
<213> ORGANISM: Artificial
<220> FEATURE:
<223> OTHER INFORMATION: human HTT siRNA

<400> SEQUENCE: 53
cccucaucca cugugugca                                                   19

<210> SEQ ID NO 54
<211> LENGTH: 19
<212> TYPE: RNA
<213> ORGANISM: Artificial
<220> FEATURE:
<223> OTHER INFORMATION: human HTT siRNA

<400> SEQUENCE: 54
ugcacacagu ggaugaggg                                                   19

<210> SEQ ID NO 55
<211> LENGTH: 19
<212> TYPE: RNA
<213> ORGANISM: Artificial
<220> FEATURE:
<223> OTHER INFORMATION: human HTT siRNA

<400> SEQUENCE: 55
cccucaucca cucugugca                                                   19

<210> SEQ ID NO 56
<211> LENGTH: 19
<212> TYPE: RNA
<213> ORGANISM: Artificial
<220> FEATURE:
<223> OTHER INFORMATION: human HTT siRNA

<400> SEQUENCE: 56
ugcacagagu ggaugaggg                                                   19

<210> SEQ ID NO 57
<211> LENGTH: 19
<212> TYPE: RNA
<213> ORGANISM: Artificial
<220> FEATURE:
<223> OTHER INFORMATION: human HTT siRNA

<400> SEQUENCE: 57
cccucaucca cugagugca                                                   19

<210> SEQ ID NO 58
<211> LENGTH: 19
<212> TYPE: RNA
<213> ORGANISM: Artificial
<220> FEATURE:
<223> OTHER INFORMATION: human HTT siRNA

<400> SEQUENCE: 58
ugcacucagu ggaugaggg                                                   19

<210> SEQ ID NO 59
```

```
<211> LENGTH: 19
<212> TYPE: RNA
<213> ORGANISM: Artificial
<220> FEATURE:
<223> OTHER INFORMATION: human HTT siRNA

<400> SEQUENCE: 59
cccucaucca cugucugca                                                        19

<210> SEQ ID NO 60
<211> LENGTH: 19
<212> TYPE: RNA
<213> ORGANISM: Artificial
<220> FEATURE:
<223> OTHER INFORMATION: human HTT siRNA

<400> SEQUENCE: 60
ugcagacagu ggaugaggg                                                        19

<210> SEQ ID NO 61
<211> LENGTH: 19
<212> TYPE: RNA
<213> ORGANISM: Artificial
<220> FEATURE:
<223> OTHER INFORMATION: human HTT siRNA

<400> SEQUENCE: 61
cccucaucca cugugagca                                                        19

<210> SEQ ID NO 62
<211> LENGTH: 19
<212> TYPE: RNA
<213> ORGANISM: Artificial
<220> FEATURE:
<223> OTHER INFORMATION: human HTT siRNA

<400> SEQUENCE: 62
ugcucacagu ggaugaggg                                                        19

<210> SEQ ID NO 63
<211> LENGTH: 19
<212> TYPE: RNA
<213> ORGANISM: Artificial
<220> FEATURE:
<223> OTHER INFORMATION: human HTT siRNA

<400> SEQUENCE: 63
cccucaucca cugugucca                                                        19

<210> SEQ ID NO 64
<211> LENGTH: 19
<212> TYPE: RNA
<213> ORGANISM: Artificial
<220> FEATURE:
<223> OTHER INFORMATION: human HTT siRNA

<400> SEQUENCE: 64
uggacacagu ggaugaggg                                                        19

<210> SEQ ID NO 65
<211> LENGTH: 19
<212> TYPE: RNA
<213> ORGANISM: Artificial
<220> FEATURE:
<223> OTHER INFORMATION: human HTT siRNA

<400> SEQUENCE: 65
```

```
ggguuucucc gcucagccu                                               19

<210> SEQ ID NO 66
<211> LENGTH: 19
<212> TYPE: RNA
<213> ORGANISM: Artificial
<220> FEATURE:
<223> OTHER INFORMATION: human HTT siRNA

<400> SEQUENCE: 66
aggcugagcg gagaaaccc                                               19

<210> SEQ ID NO 67
<211> LENGTH: 19
<212> TYPE: RNA
<213> ORGANISM: Artificial
<220> FEATURE:
<223> OTHER INFORMATION: human HTT siRNA

<400> SEQUENCE: 67
ggguuucucc gcacagccu                                               19

<210> SEQ ID NO 68
<211> LENGTH: 19
<212> TYPE: RNA
<213> ORGANISM: Artificial
<220> FEATURE:
<223> OTHER INFORMATION: human HTT siRNA

<400> SEQUENCE: 68
aggcugugcg gagaaaccc                                               19

<210> SEQ ID NO 69
<211> LENGTH: 19
<212> TYPE: RNA
<213> ORGANISM: Artificial
<220> FEATURE:
<223> OTHER INFORMATION: human HTT siRNA

<400> SEQUENCE: 69
ggguuucucc gcugagccu                                               19

<210> SEQ ID NO 70
<211> LENGTH: 19
<212> TYPE: RNA
<213> ORGANISM: Artificial
<220> FEATURE:
<223> OTHER INFORMATION: human HTT siRNA

<400> SEQUENCE: 70
aggcucagcg gagaaaccc                                               19

<210> SEQ ID NO 71
<211> LENGTH: 41
<212> TYPE: DNA
<213> ORGANISM: Homo sapiens
<220> FEATURE:
<223> OTHER INFORMATION: human HTT fragment

<400> SEQUENCE: 71
ctagcatgcg tttggagggt ttctccgctc agccttggat a                      41

<210> SEQ ID NO 72
<211> LENGTH: 41
<212> TYPE: DNA
```

```
<213> ORGANISM: Homo sapiens
<220> FEATURE:
<223> OTHER INFORMATION: human HTT fragment

<400> SEQUENCE: 72
ggcctatcca aggctgagcg gagaaaccct ccaaacgcat g                     41

<210> SEQ ID NO 73
<211> LENGTH: 41
<212> TYPE: DNA
<213> ORGANISM: Homo sapiens
<220> FEATURE:
<223> OTHER INFORMATION: human HTT fragment

<400> SEQUENCE: 73
ctagcatgcg tttggagggt ttcttcgctc agccttggat a                     41

<210> SEQ ID NO 74
<211> LENGTH: 41
<212> TYPE: DNA
<213> ORGANISM: Homo sapiens
<220> FEATURE:
<223> OTHER INFORMATION: human HTT fragment

<400> SEQUENCE: 74
ggcctatcca aggctgagcg aagaaaccct ccaaacgcat g                     41

<210> SEQ ID NO 75
<211> LENGTH: 41
<212> TYPE: DNA
<213> ORGANISM: Homo sapiens
<220> FEATURE:
<223> OTHER INFORMATION: human HTT fragment

<400> SEQUENCE: 75
ctagcatgcg cctgctccct catccactgt gtgcacttca a                     41

<210> SEQ ID NO 76
<211> LENGTH: 41
<212> TYPE: DNA
<213> ORGANISM: Homo sapiens
<220> FEATURE:
<223> OTHER INFORMATION: human HTT fragment

<400> SEQUENCE: 76
ggccttgaag tgcacacagt ggatgaggga gcaggcgcat g                     41

<210> SEQ ID NO 77
<211> LENGTH: 41
<212> TYPE: DNA
<213> ORGANISM: Homo sapiens
<220> FEATURE:
<223> OTHER INFORMATION: human HTT fragment

<400> SEQUENCE: 77
ctagcatgcg cctgctccct catctactgt gtgcacttca a                     41

<210> SEQ ID NO 78
<211> LENGTH: 41
<212> TYPE: DNA
<213> ORGANISM: Homo sapiens
<220> FEATURE:
<223> OTHER INFORMATION: human HTT fragment

<400> SEQUENCE: 78
ggccttgaag tgcacacagt agatgaggga gcaggcgcat g                     41
```

```
<210> SEQ ID NO 79
<211> LENGTH: 18
<212> TYPE: RNA
<213> ORGANISM: Artificial
<220> FEATURE:
<223> OTHER INFORMATION: human EGFR siRNA

<400> SEQUENCE: 79
gcucaucaug cagcucau                                                 18

<210> SEQ ID NO 80
<211> LENGTH: 18
<212> TYPE: RNA
<213> ORGANISM: Artificial
<220> FEATURE:
<223> OTHER INFORMATION: human EGFR siRNA

<400> SEQUENCE: 80
augagcugca ugaugagc                                                 18

<210> SEQ ID NO 81
<211> LENGTH: 18
<212> TYPE: RNA
<213> ORGANISM: Artificial
<220> FEATURE:
<223> OTHER INFORMATION: human EGFR siRNA

<400> SEQUENCE: 81
gcucaucaug caccucau                                                 18

<210> SEQ ID NO 82
<211> LENGTH: 18
<212> TYPE: RNA
<213> ORGANISM: Artificial
<220> FEATURE:
<223> OTHER INFORMATION: human EGFR siRNA

<400> SEQUENCE: 82
augaggugca ugaugagc                                                 18

<210> SEQ ID NO 83
<211> LENGTH: 18
<212> TYPE: RNA
<213> ORGANISM: Artificial
<220> FEATURE:
<223> OTHER INFORMATION: human EGFR siRNA

<400> SEQUENCE: 83
gcucaucaug cagcacau                                                 18

<210> SEQ ID NO 84
<211> LENGTH: 18
<212> TYPE: RNA
<213> ORGANISM: Artificial
<220> FEATURE:
<223> OTHER INFORMATION: human EGFR siRNA

<400> SEQUENCE: 84
augugcugca ugaugagc                                                 18

<210> SEQ ID NO 85
<211> LENGTH: 35
<212> TYPE: DNA
<213> ORGANISM: Homo sapiens
<220> FEATURE:
```

```
<223> OTHER INFORMATION: human EGFR fragment

<400> SEQUENCE: 85
ctagcatgcg tgcagctcat catgcagctc atgca                              35

<210> SEQ ID NO 86
<211> LENGTH: 35
<212> TYPE: DNA
<213> ORGANISM: Homo sapiens
<220> FEATURE:
<223> OTHER INFORMATION: human EGFR fragment

<400> SEQUENCE: 86
ggcctgcatg agctgcatga tgagctgcac gcatg                              35

<210> SEQ ID NO 87
<211> LENGTH: 35
<212> TYPE: DNA
<213> ORGANISM: Homo sapiens
<220> FEATURE:
<223> OTHER INFORMATION: human EGFR fragment

<400> SEQUENCE: 87
ctagcatgcg tgcagctcat cacgcagctc atgca                              35

<210> SEQ ID NO 88
<211> LENGTH: 35
<212> TYPE: DNA
<213> ORGANISM: Homo sapiens
<220> FEATURE:
<223> OTHER INFORMATION: human EGFR fragment

<400> SEQUENCE: 88
ggcctgcatg agctgcgtga tgagctgcac gcatg                              35

<210> SEQ ID NO 89
<211> LENGTH: 19
<212> TYPE: RNA
<213> ORGANISM: Artificial
<220> FEATURE:
<223> OTHER INFORMATION: human ALK2 siRNA

<400> SEQUENCE: 89
caguggcuca ccagauuac                                                19

<210> SEQ ID NO 90
<211> LENGTH: 19
<212> TYPE: RNA
<213> ORGANISM: Artificial
<220> FEATURE:
<223> OTHER INFORMATION: human ALK2 siRNA

<400> SEQUENCE: 90
guaaucuggu gagccacug                                                19

<210> SEQ ID NO 91
<211> LENGTH: 19
<212> TYPE: RNA
<213> ORGANISM: Artificial
<220> FEATURE:
<223> OTHER INFORMATION: human ALK2 siRNA

<400> SEQUENCE: 91
caguggcuca ccugauuac                                                19
```

```
<210> SEQ ID NO 92
<211> LENGTH: 19
<212> TYPE: RNA
<213> ORGANISM: Artificial
<220> FEATURE:
<223> OTHER INFORMATION: human ALK2 siRNA

<400> SEQUENCE: 92
guaaucaggu gagccacug                                              19
```

AGENT FOR SUPPRESSING EXPRESSION OF DOMINANT ALLELE

RELATED APPLICATIONS

This application is a national stage application filed under 35 USC §371 of PCT/JP2011/068378, filed Jun. 17, 2011, which claims the benefit of Japanese Patent Application No. 2010-0139925, filed Jun. 18, 2010, both of which are incorporated herein, in entirety, by reference.

TECHNICAL FIELD

The present invention relates to an agent for suppressing the expression of a dominant allele, comprising an RNAi molecule that can selectively and effectively suppress the expression of a mutant allele containing a dominant point mutation, a pharmaceutical composition comprising the expression-suppressing agent, and a method for designing an RNAi molecule.

BACKGROUND ART

In recent years, functional nucleic acids controlling the expression of particular genes in vivo have received attention as novel pharmaceutical drugs or diagnostic drugs comparable to compounds and antibodies. Various studies and developments toward medical applications thereof are underway around the world.

The known functional nucleic acids include, for example: small interfering RNAs (siRNAs), short hairpin RNAs (shRNAs), and micro RNAs (miRNAs), which post-transcriptionally suppress the expression of target genes by gene silencing mediated by RNA interference (RNAi); nucleic acid aptamers, which suppress the functions of target substances such as transcription factors by specifically binding thereto; antisense nucleic acids, which suppress the translation of target mRNAs by binding thereto; decoy DNAs containing regulatory regions such as transcription factor-binding domains as decoy sequences, wherein the decoy DNAs capture target substances, thereby suppressing gene expression caused by the transcription factors; and UI adaptors, which specifically inhibit polyadenylation in the mRNA precursors of target genes to destabilize the mRNA molecules and then direct the degradation thereof. All of them are expected as the next-generation pharmaceutical drugs or diagnostic drugs. Among them, RNAi by siRNAs or shRNAs is in the limelight as powerful gene expression control tools capable of suppressing the desired gene expression, because of their target specificity, wide applications, and reliable effects.

Allele-specific gene silencing (or allele-specific RNAi: ASP-RNAi), which is the application of RNAi, can specifically suppress the expression of a desired allele and can therefore specifically suppress only the expression of a mutant allele causing a disease without influencing the expression of wild-type alleles. Hence, this method is considered exceedingly useful in disease therapy.

For example, fibrodysplasia ossificans progressiva (FOP) known as an intractable autosomal dominantly inherited disease is caused by a point mutation that substitutes guanine (G) at the 617th position by adenine (A) or a point mutation that substitutes G at the 1067th point by A on its causative activin-like kinase 2 (ALK2) gene. Since an allele having any of these point mutations is dominant, even a heterozygote having wild-type ALK2 gene is known to develop FOP (Non Patent Literatures 1 to 3). Unfortunately, an effective method for suppressing the onset or progression of this disease has not yet been found. The same holds true for many other autosomal dominantly inherited diseases caused by point mutations. In this context, if ASP-RNAi can suppress only the expression of a mutant allele having a point mutation and permit the expression of wild-type alleles, the onset of autosomal dominantly inherited diseases including FOP can be suppressed. In addition, the progression of these diseases can be prevented for patients who have already developed the diseases.

Such a mutant allele having a point mutation and the wild-type allele differ in their nucleotide sequences only by one to several bases. Thus, the development of siRNAs or shRNAs having exceedingly high specificity is essential for achieving such ASP-RNAi. Nevertheless, regions for designing siRNAs or the like are inevitably limited, because a point mutation site and its neighboring nucleotide sequences are to be used as a target region. Hence, effective methods for selecting target sequences of siRNAs known in the art cannot always be applied to the design. As a result, the design may disadvantageously fail to constantly produce highly specific and effective siRNAs or the like.

In an attempt to develop siRNAs or the like having exceedingly high specificity, it is disadvantageously difficult to correctly discriminate between mutant alleles and wild-type alleles for ASP-RNAi and quantitatively evaluate suppressive effects on their respective expressions.

Non Patent Literature 4 discloses a reporter system using luciferase gene. The literature also proposes a guideline for the design of siRNAs that involves quantifying a suppressive effect on the expression of a mutant allele using this system and bringing about ASP-RNAi on the basis of the obtained results. The accurate evaluation of an ASP-RNAi effect usually requires accurately discriminating between wild-type alleles and mutant alleles and precisely suppressing the expression of the mutant alleles of interest. This requires evaluating suppressive effects on the respective expressions of wild-type alleles and mutant alleles within the same cell. However, the reporter system used in the literature independently detects only the suppression of the expression of a mutant allele. The influence of the siRNAs on wild-type alleles was not sufficiently verified. Thus, the guideline for allele-specific siRNAs obtained using the reporter system disclosed in the literature was not sufficient in terms of accuracy and effects.

Meanwhile, the present inventors have developed a reporter allele evaluation system using *Photinus* luciferase gene and *Renilla* luciferase gene having high substrate specificity and disclosed it in Non Patent Literature 5. According to the system, siRNAs and expression vectors each carrying the sequence of a target mutant allele or the sequence of a non-target wild-type allele inserted to the 3' UTR of the luciferase gene are cotransfected into cultured cells, and luciferase activity derived from each expression vector can be detected on the basis of luminescence, thereby specifically quantifying suppression efficiency for the respective expressions of the mutant allele and the wild-type allele by the siRNAs within the same cell. Thus, use of the reporter allele evaluation system allows more accurate evaluation of an ASP-RNAi effect or development of siRNAs or the like having a higher ASP-RNAi effect.

Non Patent Literature 6 describes, as a specific example of ASP-RNAi evaluation using the reporter allele evaluation system, results of designing an siRNA or shRNA against a mutant allele of human prion gene so that its sequence artificially contains a mismatch mutation at one position and variously changing its base length and the position of the mismatch mutation. The method of this literature produces a relatively marked ASP-RNAi effect. This experiment, however, employed only the human prion gene. In general, the effect of RNAi largely depends on the targeting nucleotide sequence against the target gene, i.e., the target gene-homologous nucleotide sequence incorporated in the siRNA or shRNA. Even if the introduced mismatch mutation can improve an ASP-RNAi effect, this effect is likely to be unique to the targeting nucleotide sequence used in the experiment and cannot be generalized. Accordingly, the results of Non Patent Literature 5 have not led to a guideline for the design of siRNAs or shRNAs having a high ASP-RNAi effect.

CITATION LIST

Non Patent Literature

Non Patent Literature 1: Shore E M., et al., 2006, Nature Genetics, Vol. 38: 525-527
Non Patent Literature 2: Nakajima M., et al., 2007, Journal of Human Genetics, Vol. 52: 473-475
Non Patent Literature 3: Furuya H., et al., 2008, American Journal of Medical Genetics Part A,
Vol. 146A: 459-463
Non Patent Literature 4: Huang H., et al. 2009, Nucleic Acids Research, Vol. 37: 7560-7569
Non Patent Literature 5: Ohnishi Y., et al., 2006, Journal of RNAi and Gene Silencing, Vol. 2: 154-160
Non Patent Literature 6: Ohnishi Y., et al., 2008, PloS One, Vol. 3, Issue 5: e2248

SUMMARY OF INVENTION

Technical Problem

An object of the present invention is to develop an RNAi molecule that permits the expression of wild-type or desired alleles and can selectively and effectively suppress only the expression of a particular dominant allele and to provide a guideline for design thereof and an agent for suppressing the expression of a dominant allele, comprising the RNAi molecule as an active ingredient.

Another object of the present invention is to provide a therapeutic agent that treats an inherited disease developed by the expression of a dominant allele.

Solution to Problem

As a result of conducting diligent studies to attain the objects, the present inventors have found the general structural rule of siRNAs, etc. capable of selectively and effectively suppressing the expression of particular alleles. Specifically, an RNAi molecule having a structure obtained by assigning a dominant point mutation in the targeted dominant allele as a standard point, setting a base length from the standard point to the 5' end to a predetermined length, and introducing one mismatch base different from the corresponding base in the sequence of the target gene, to a predetermined position downstream from the standard point, has been shown to selectively and effectively suppress the expression of the dominant allele, but hardly exhibit a suppressive effect on the expression of the other alleles including wild-type alleles. The RNAi molecule having such a structure has also been shown to be capable of exerting its effects on any allele, irrespective of its nucleotide sequence. Thus, this structure presumably serves as a novel guideline for ASP-RNAi. The present invention has been completed on the basis of these findings and provides the followings:

(1) An agent for suppressing the expression of a dominant allele of a target gene, comprising an RNAi molecule, the RNAi molecule comprising an RNAi sense strand region and an RNAi antisense strand region consisting of a nucleotide sequence complementary thereto, the RNAi sense strand region consisting of a nucleotide sequence substantially identical to any one 16- to 30-base consecutive nucleotide sequence in the sense strand of the dominant allele comprising at least one dominant point mutation, wherein: any one base at the 7th to 10th positions upstream from any one dominant point mutation in the RNAi sense strand region constitutes the 5'-terminal base of the RNAi molecule; and any one base at the 3rd to 8th positions downstream from the any one dominant point mutation is the only mismatch base different from the corresponding base in the nucleotide sequence in the sense strand of the dominant allele.

(2) An agent for suppressing the expression of a dominant allele of a target gene, comprising an expression vector comprising an operably linked DNA encoding an RNAi molecule, the RNAi molecule comprising an RNAi sense strand region and an RNAi antisense strand region consisting of a nucleotide sequence complementary thereto, the RNAi molecule consisting of a nucleotide sequence substantially identical to any one 16- to 30-base consecutive nucleotide sequence in the sense strand of the dominant allele comprising at least one dominant point mutation, wherein: any one base at the 7th to 10th positions upstream from any one dominant point mutation in the RNAi sense strand region constitutes the 5'-terminal base of the RNAi molecule; and any one base at the 3rd to 8th positions downstream from the any one dominant point mutation is a mismatch base different from the corresponding base in the nucleotide sequence in the sense strand of the dominant allele.

(3) The suppressing agent according to (1) or (2), wherein the base constituting the 5'-terminal base is any one base at the 7th to 9th positions upstream from the dominant point mutation.

(4) The suppressing agent according to any of (1) to (3), wherein the mismatch base is any one base at the 3rd to 5th positions downstream from the dominant point mutation.

(5) The suppressing agent according to any of (1) to (4), wherein the RNAi molecule is an siRNA.

(6) The suppressing agent according to any of (1) to (4), wherein the RNAi molecule is an shRNA.

(7) The suppressing agent according to any of (1) to (6), wherein the dominant point mutation is a gain-of-function mutation.

(8) The suppressing agent according to any of (1) to (7), wherein the dominant point mutation is involved in the onset of a disease.

(9) The suppressing agent according to (8), wherein the disease is a malignant neoplasm.

(10) The suppressing agent according to (9), wherein the malignant neoplasm is non-small cell lung cancer, and the target gene is epidermal growth factor receptor (EGFR) gene.

(11) The suppressing agent according to (10), wherein the sense and antisense strands of the RNAi molecule consist of an oligonucleotide pair shown in SEQ ID NOs: 81 and 82 or SEQ ID NOs: 83 and 84, respectively.

(12) The suppressing agent according to (8), wherein the disease is fibrodysplasia ossificans progressiva, and the target gene is activin-like kinase 2 (ALK2) gene.

(13) The suppressing agent according to (12), wherein the sense and antisense strands of the RNAi molecule are selected from the group consisting of oligonucleotide pairs shown in SEQ ID NOs: 3 and 4, SEQ ID NOs: 5 and 6, SEQ ID NOs: 7 and 8, SEQ ID NOs: 9 and 10, SEQ ID NOs: 11 and 12, SEQ ID NOs: 13 and 14, SEQ ID NOs: 19 and 20, SEQ ID NOs: 21 and 22, SEQ ID NOs: 23 and 24, SEQ ID NOs: 25 and 26, SEQ ID NOs: 27 and 28, SEQ ID NOs: 29 and 30, SEQ ID NOs: 35 and 36, SEQ ID NOs: 37 and 38, SEQ ID NOs: 39 and 40, SEQ ID NOs: 41 and 42, SEQ ID NOs: 43 and 44, and SEQ ID NOs: 91 and 92, respectively.

(14) The suppressing agent according to (8), wherein the disease is Huntington's disease, and the target gene is huntingtin gene.

(15) The suppressing agent according to (14), wherein the sense and antisense strands of the RNAi molecule are selected from the group consisting of oligonucleotide pairs shown in SEQ ID NOs: 55 and 56, SEQ ID NOs: 57 and 58, SEQ ID NOs: 59 and 60, SEQ ID NOs: 61 and 62, SEQ ID NOs: 63 and 64, SEQ ID NOs: 67 and 68, and SEQ ID NOs: 69 and 70, respectively.

(16) A pharmaceutical composition comprising a suppressing agent according to any one of (1) to (15) as an active ingredient.

(17) The pharmaceutical composition according to (16), further comprising a pharmaceutically acceptable carrier.

(18) A method for designing an RNAi molecule selectively suppressing the expression of a dominant allele of a target gene, comprising the steps of: assigning one dominant point mutation site present in the nucleotide sequence of the dominant allele of a target gene as a standard mutation point; assigning any one base at the 7th to 10th positions upstream from the standard mutation point in the nucleotide sequence of the dominant allele as a 5'-terminal base; selecting downstream 16 to 30 bases starting at the assigned 5'-terminal base as an RNAi sense strand region from a nucleotide sequence in the sense strand of the dominant allele; and introducing a mismatch base to any one base at the 3rd to 8th positions downstream from the standard mutation point within the selected RNAi sense strand region.

Advantageous Effects of Invention

The agent for suppressing the expression of a dominant allele according to the present invention can selectively and effectively suppress only the expression of the targeted dominant allele without largely influencing the expression of the other alleles.

A method for designing an RNAi molecule serving as an active ingredient in the agent for suppressing the expression of a dominant allele according to the present invention can provide a highly applicable design method that is capable of designing the RNAi molecule with a dominant point mutation responsible for a disease as a standard point without being largely influenced by neighboring nucleotide sequences of the standard point.

The pharmaceutical composition of the present invention can cure an inherited disease by selectively suppressing the expression of a dominant allele responsible for the disease while maintaining the expression of wild-type alleles.

BRIEF DESCRIPTION OF DRAWINGS

FIG. 1(A) shows a double-stranded RNAi molecule (siRNA), and FIG. 1(B) shows a single-stranded RNAi molecule (shRNA).

FIG. 3A shows the discrimination ratio (plot) and ASP score (bar graph) of each ALK2-G356D-siRNA used. FIG. 3B shows relative luciferase expression levels representing the expression of a non-target wild-type ALK2 (WT-ALK2) fragment and a target mutant ALK2 (MT-ALK2) fragment.

FIG. 4A shows the discrimination ratio (plot) and ASP score (bar graph) of each ALK2-G356D-siRNA used. FIG. 4B shows relative luciferase expression levels representing the expression of a non-target wild-type ALK2 sequence (WT-ALK2) fragment and a target mutant ALK2 sequence (MT-ALK2) fragment.

FIGS. 5A and 5C show Western blotting results, and FIGS. 5B and 5D show numbers converted from the bands of FIGS. 5A and 5C, respectively. MT in FIGS. 5A and 5B represents ALK2 containing a R206H point mutation, and MT in FIGS. 5C and 5D represents ALK2 containing a G356D point mutation. In the diagram, the symbol ** represents being statistically significant ($p<0.01$). The symbol n.s. represents being not statistically significant. The symbol siControl represents a control siRNA (Qiagen) that does not induce RNAi.

FIG. 6A shows the discrimination ratio (plot) and ASP score (bar graph) of each HTT-siRNA used. FIG. 6B shows relative luciferase expression levels representing the expression of a non-target wild-type HTT fragment and a mutant HTT fragment.

FIG. 8A shows the discrimination ratio (plot) and ASP score (bar graph) of each EGFR-siRNA used. FIG. 8B shows relative luciferase expression levels representing the expression of a wild-type EGFR (T790T) fragment and a mutant EGFR (T790M) fragment.

DESCRIPTION OF EMBODIMENTS

Figure 1:
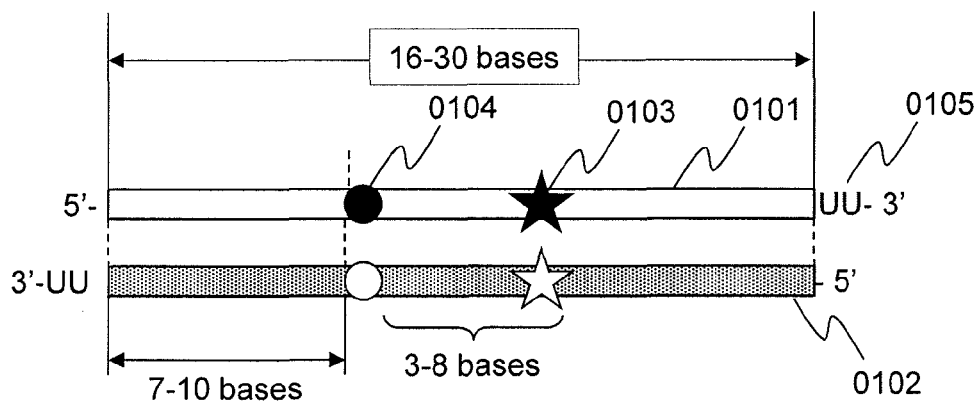
FIG. 1 shows a conceptual diagram of the structure of an RNAi molecule.
Figure 1:
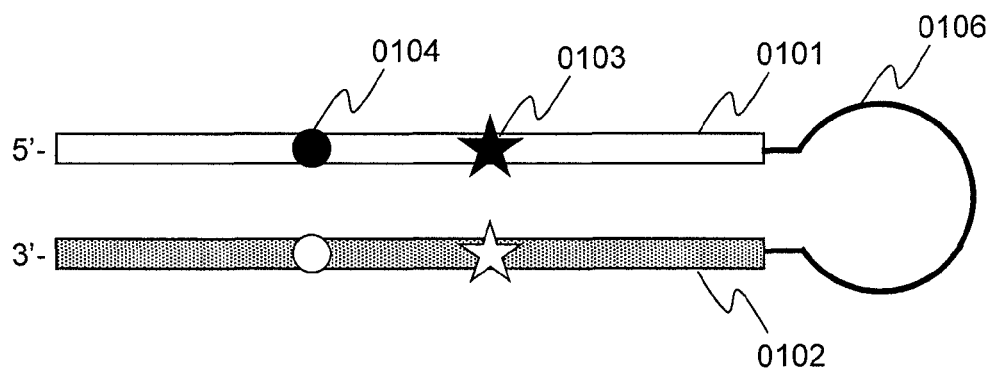

1. Agent for Suppressing Expression of Dominant Allele
1-1. Summary

The first aspect of the present invention relates to an agent for suppressing the expression of a dominant allele. The suppressing agent of the present invention comprises an RNAi molecule and/or an expression vector encoding it as an active ingredient, wherein the RNAi molecule targets the dominant allele and selectively suppresses the expression thereof.

1-2. Constitution of RNAi Molecule

In the present specification, the "RNAi molecule" refers to a molecule that is capable of inducing RNA interference in vivo to post-transcriptionally and pre-translationally suppress (silence) the expression of a targeted gene via the degradation of the gene transcript. The RNAi molecule may be single-stranded or double-stranded as long as the molecule can suppress the gene expression of interest through the RNAi mechanism. Examples thereof include double-stranded molecules such as siRNAs, and single-stranded molecules such as shRNAs and miRNAs. For the RNA interference, see, for example, Bass B. L., 2000, Cell, 101, 235-238;

Sharp P. A., 2001, Genes Dev., 15, 485-490; Zamore P. D., 2002, Science, 296, 1265-1269; and Dernburg, A. F. & Karpen, G. H., 2002, Cell, 111, 159-162. In the present specification, hereinafter, the post-transcriptional gene silencing mediated by the RNAi mechanism is referred to as the "suppression of gene expression".

In the present specification, the RNAi molecule consists of a nucleic acid. In this context, the "nucleic acid" refers to a natural nucleic acid, a non-natural nucleic acid, and/or a nucleic acid analog.

In the present specification, the "natural nucleic acid" refers to a naturally occurring biological polymer that is constituted of nucleotide units linked through phosphodiester bonds. The natural nucleic acid typically corresponds to an RNA comprising an assembly of ribonucleotides having any of the bases adenine, guanine, cytosine, and uracil, and/or a DNA comprising an assembly of deoxyribonucleotides having any of the bases adenine, guanine, cytosine, and thymine. The RNAi molecule of the present invention is preferably composed mainly of, particularly, RNA.

In the present specification, the "non-natural nucleic acid" refers to a nucleic acid comprising or consisting of non-natural nucleotides. In this context, the "non-natural nucleotides" refer to artificially constructed or artificially chemically modified nucleotides that are not found in the natural world and refer to nucleotides similar in properties and/or structure to the naturally occurring nucleotides, or nucleotides comprising nucleosides or bases similar in properties and/or structure to naturally occurring nucleosides or bases. Examples thereof include abasic nucleoside, arabinonucleoside, 2'-deoxyuridine, α-deoxyribonucleoside, β-L-deoxyribonucleoside, and other nucleosides having sugar modification. Such nucleosides further include nucleosides having substituted pentose (2'-O-methylribose, 2'-deoxy-2'-fluororibose, 3'-O-methylribose, or 1',2'-deoxyribose), arabinose, or substituted arabinose sugar; or substituted hexose, or sugar modification resulting in an alpha anomer. The non-natural nucleotides also include nucleotides containing artificially constructed base analogs or artificially chemically modified bases (modified bases). Examples of the "base analogs" include a 2-oxo(1H)-pyridin-3-yl group, a 5-substituted 2-oxo(1H)-pyridin-3-yl group, a 2-amino-6-(2-thiazolyl)purin-9-yl group, a 2-amino-6-(2-thiazolyl)purin-9-yl group, and a 2-amino-6-(2-oxazolyl)purin-9-yl group. Examples of the "modified bases" include modified pyrimidine (e.g., 5-hydroxycytosine, 5-fluorouracil, and 4-thiouracil), modified purine (e.g., 6-methyladenine and 6-thioguanosine), and other heterocyclic bases. The non-natural nucleic acid can also include chemically modified nucleic acids or nucleic acid analogs such as methylphosphonate-type DNA or RNA, phosphorothioate-type DNA or RNA, phosphoramidate-type DNA or RNA, and 2'-O-methyl-type DNA or RNA.

In the present specification the "nucleic acid analog" refers to an artificially constructed compound similar in structure and/or properties to the natural nucleic acid. Examples thereof include a peptide nucleic acid (PNA), a peptide nucleic acid having a phosphate group (PHONA), a bridged nucleic acid or locked nucleic acid (BNA or LNA), and a morpholino nucleic acid.

The nucleic acid constituting the RNAi molecule of the present invention may be labeled at its phosphate group, sugar, and/or base, if necessary, with a labeling material for nucleic acids. Any substance known in the art can be used as the labeling material for nucleic acids. Examples thereof include radioisotopes (e.g., $^{32}P$, $^{3}H$, and $^{14}C$), DIG, biotin, fluorescent dyes (e.g., FITC, Texas, cy3, cy5, cy7, FAM, HEX, VIC, JOE, Rox, TET, Bodipy 493, NBD, and TAMRA), and luminescent materials (e.g., acridinium ester).

The "alleles", also called allelomorphs, refer to individual forms of a gene that reside at homologous loci on the genome and constitute polymorphisms, as a rule. In this regard, the alleles are not necessarily required to reside at homologous loci as long as they constitute the polymorphisms of the same gene. The alleles may reside at different loci due to translocation or redundancy. In the present invention, the alleles include those congenitally residing on the genome as well as those postnatally acquired by mutation. Each allele does not have to reside in all cells constituting an individual and may reside only in some cells, tissues, or organs in the individual. Examples of such an allele include mutant alleles that do not reside in normal cells but reside only in cancer cells in one individual.

In the present specification, the "dominant allele" refers to an allele from which a trait is preferentially manifested as a phenotype in the individual. In the case of, for example, two different alleles on diploid chromosomes, the dominant allele corresponds to one of the alleles, from which a trait observably appears in the individual. The alleles may or may not encode proteins having normal functions. For example, one of the alleles may encode an abnormally functioning protein while the other allele may encode a normally functioning protein. In this case, the allele encoding the abnormally functioning protein works as a dominant allele when the abnormal function of the abnormally functioning protein excels or inhibits the function of the normally functioning protein, resulting in the abnormal function of the protein exhibited as a phenotype in the individual. Specific examples thereof include alleles responsible for autosomal dominantly inherited diseases.

In the present specification, the "point mutation" refers to a single-base substitution observed in a nucleotide sequence compared with the corresponding nucleotide sequence of a wild-type allele. In this context, the "wild-type allele" refers to the most commonly naturally occurring allele in the allele population of the same type of gene, wherein a protein encoded by this allele has its original functions. The point mutation typically includes a transition mutation that substitutes purine by another purine or substitutes pyrimidine by another pyrimidine, and a transversion mutation that substitutes purine by pyrimidine or vice versa. In the present invention, any of these mutations may be used. The point mutation of the present invention may be any of congenitally occurring mutations and postnatally acquired mutations. Further known point mutations are a missense mutation that brings about amino acid substitution, a silent mutation that does not result in amino acid substitution but causes change to a degenerate codon, a nonsense mutation that leads to the appearance of a stop codon, and a mutation at a splicing site. For the RNAi molecule of the present invention, the point mutation is preferably a missense mutation, a nonsense mutation, or a mutation at a splicing site.

The "dominant point mutation" refers to a point mutation that confers a dominant trait on the allele, or a dominant mutation-associated (or -linked) point mutation in one transcript. The dominant mutation-associated point mutation in one transcript corresponds to, for example, a single-nucleotide polymorphism (SNP) site associated with a dominant mutation such as an abnormally expanded triplet repeat sequence that brings about a dominant trait, typically, in triplet repeat disease. In the present invention, the properties of the dominant point mutation are not particularly limited. Examples of the point mutation that confers a dominant trait include a gain-of-function mutation and a loss-of-function mutation. The gain-of-function mutation includes: a hypermorph mutation resulting in a trait that exhibits increased amount (overexpression) or increased activity (constitutive activity or hyperactivity) of a protein; a neomorph mutation resulting in a trait that exhibits novel functional activity; and an antimorph mutation (dominant negative) resulting in the suppressed exhibition of a trait of a wild-type allele because the gene product antagonizes or suppresses a protein derived from the wild-type allele. Examples of the loss-of-function mutation include: an amorph mutation in which the resulting allele is completely unable to express its trait; and a hypomorph mutation in which the resulting allele is less able to express its trait. In this regard, the loss-of-function mutation is limited to those producing dominant effects. The dominant point mutation is preferably a gain-of-function mutation. The dominant mutation-associated point mutation in one transcript is not particularly limited and may be, for example, a mutation that does not result in amino acid substitution, such as SNP leading to a degeneracy mutation. The targeted dominant allele may have one or more dominant point mutation(s) on its nucleotide sequence.

In the present aspect, the type of a targeted gene and an organism species from which the gene is derived are not particularly limited. A gene encoding any protein can be targeted by the suppressing agent of the present aspect as long as its dominant allele comprises the dominant point mutation(s). Also, the organism species may be any of animals and plants and encompasses any type thereof. The animal is preferably a vertebrate, more preferably fish, a bird, or a mammal. The fish is particularly preferably a fish species for marine resources (e.g., fish species of the families Salmonidae, Serranidae, Gadidae, Clupeidae, Paralichthyidae, Pleuronectidae, Carangidae, Ammodytidae, Sparidae, and Sebastidae). The bird is particularly preferably an edible species (e.g., chickens, geese, domestic ducks, ducks, mallards, turkeys, quails, and ostriches). The mammal is particularly preferable livestock (pigs, cattle, sheep, goats, and horses), a laboratory animal (rodents, rabbits, dogs, and monkeys), a racehorse, a pet animal (dogs, cats, rabbits, monkeys, and rodents), or a human. The organism species is further preferably a human. Alternatively, the plant is preferably a seed plant, more preferably an angiosperm, further preferably an edible plant species (e.g., edible plant species belonging to the families Poaceae, Leguminosae, Solanaceae, Convolvulaceae, Rosaceae, Brassicaceae, Chenopodiaceae, Umbelliferae, Polygonaceae, Cucurbitaceae, Compositae, Liliaceae, Araceae, Vitaceae, Rutaceae, Fagaceae, and Arecaceae), a plant species for fiber resources (e.g., cotton and hemp), or a plant species for wood resources (e.g., Japanese cedar, cypress, fir, hemlock fir, pine, yew, cherry, maple, live oak, oak, beech, elm, zelkova, walnut, Japanese big-leaf magnolia, Katsura tree, teak, lauan, ebony, mahogany, poplar, and eucalyptus).

The trait in which the dominant point mutation is involved is not particularly limited and is preferably a trait whose exhibition is to be suppressed. Examples thereof include a mutation involved in the onset of a disease and a mutation involved in abnormal morphology. In this context, the disease includes the autosomal dominantly inherited diseases whose causative mutation is a point mutation or a postnatally occurring point mutation in genomic DNA within a particular cell. More specifically, examples of the autosomal dominantly inherited diseases in humans include: Huntington's disease caused by a mutation in huntingtin gene; fibrodysplasia ossificans progressiva (FOP) caused by a mutation in activin-like kinase 2 (ALK2) gene; familial amyloid polyneuropathy caused by a mutation in transthyretin gene; familial hypercholesterolemia (FH) caused by a mutation in LDL receptor (LDL-R) gene; maturity-onset diabetes of the young (MODY) caused by a mutation in each of HNF-4α gene (MODY1), glucokinase gene (MODY2), and HNF-1α gene (MODY3); Marfan's syndrome caused by a mutation in fibrin 1 gene; autosomal dominant progressive muscular dystrophy caused by a mutation in myotonin protein kinase gene; autosomal dominant osteogenesis imperfecta caused by a mutation in type I collagen gene; autosomal dominant retinitis pigmentosa caused by a mutation in rhodopsin gene or peripherin-RDS gene; autosomal dominant congenital cataract caused by a mutation in aquaporin (AQP0) gene; nodular sclerosis caused by a mutation in TSC1 or TSC2 gene; autosomal dominant polycystic kidney disease (ADPKD) caused by a mutation in PKD1 gene or PKD2 gene; hereditary palmoplantar keratoderma caused by a mutation in keratin gene, loricrin gene, desmoglein 1 gene, or desmoplakin gene; familial polyposis coli caused by a mutation in APC gene; retinoblastoma caused by a mutation in Rb gene; and neurofibroma caused by a mutation in NF1 gene. Examples of the diseases caused by a postnatally occurring point mutation in genomic DNA within a particular cell include neoplasms (tumors), particularly, malignant neoplasms (malignant tumors, so-called cancers). More specific examples thereof include non-small cell lung cancer (NSCLC) caused by a mutation in epidermal growth factor receptor (EGFR) gene, pancreatic cancer or large intestine cancer caused by a mutation in K-ras gene, and medullary thyroid cancer caused by a mutation in RET gene.

1-3. Structure of RNAi Molecule

FIG. 1 shows a conceptual diagram of the structure of the RNAi molecule contained in the suppressing agent of the present aspect. As shown in this diagram, the RNAi molecule encompasses a double-stranded molecule (FIG. 1A) and a single-stranded molecule (FIG. 1B).

(Component Common to RNAi Molecules)

Both the single-stranded and double-stranded RNAi molecules that can be contained in the suppressing agent of the present aspect comprise an RNAi sense strand region (0101), an RNAi antisense strand region (0102), and a mismatch base (0103) as essential components. Hereinafter, the components common to the RNAi molecules will be described.

The "RNAi sense strand region" (0101) refers to a nucleotide sequence identical to a nucleotide sequence in the sense strand of the dominant allele except for the mismatch base described later, wherein the nucleotide sequence has at least one dominant point mutation (0104) of the dominant allele. Since the RNAi molecule of the present aspect, as described above, is composed mainly of RNA, a base corresponding to thymine (T) in the nucleotide sequence in the sense strand of the dominant allele is uracil (U), as a rule. The base length corresponding to the nucleotide sequence in the sense strand of the dominant allele is 16 to 30 consecutive bases, 18 to 25 consecutive bases, or 19 to 23 consecutive bases. The RNAi sense strand region differs at least in the dominant point mutation site (0104) from the nucleotide sequence of the wild-type allele corresponding to the dominant allele. The RNAi sense strand region may be substantially identical to any nucleotide sequence in the sense strand of the dominant allele within the base length range described above as long as it comprises at least one dominant point mutation contained in the nucleotide sequence in the sense strand of the dominant allele.

A feature of the RNAi molecule is that a base at any of the 7th to 10th positions upstream from any one dominant point mutation (hereinafter, this dominant point mutation is referred to as a "standard mutation point") (0104) in the RNAi sense strand region corresponds to the 5'-terminal base of the RNAi sense strand region. In other words, the standard mutation point in the RNAi sense strand region is located within the 8th to 11th positions from the 5' end. In the case of an RNAi sense strand region comprising two or more dominant point mutations, the standard mutation point can be any of these dominant point mutations. In the double-stranded RNAi molecule of the present aspect (FIG. 1A), the 5'-terminal base of the RNAi sense strand region corresponds to the 5'-terminal base of one strand (polynucleotide strand) comprising the RNAi sense strand region (FIG. 1A). Alternatively, in the single-stranded RNAi molecule of the present aspect (FIG. 1B), the 5'-terminal base of the RNAi sense strand region corresponds to the 5'-terminal base of the single-stranded molecule (FIG. 1B). The distance from the standard mutation point to the 5'-terminal base in this RNAi sense strand region is an essential requirement for the constitution of the RNAi molecule of the present aspect.

The "RNAi antisense strand region" (0102) refers to a nucleotide sequence perfectly complementary to the RNAi sense strand region (0101). Thus, the RNAi antisense strand region contains, in its nucleotide sequence, a base complementary to the standard mutation point and a base complementary to the mismatch base described later. A base complementary to adenine (A) in the RNAi sense strand region is U.

In the double-stranded RNAi molecule of the present aspect (FIG. 1A), the RNAi antisense strand region is contained in another polynucleotide strand different from the polynucleotide strand comprising the RNAi sense strand region. Alternatively, in the single-stranded molecule (FIG. 1B), the RNAi antisense strand region is contained in the same polynucleotide strand as in the RNAi sense strand region.

The "mismatch base" (0103) refers to the only base that is different from the corresponding base in the nucleotide sequence in the sense strand of the dominant allele, i.e., a mismatched base in the RNAi sense strand region, wherein this base cannot base-pair with the corresponding base on the antisense strand nucleotide sequence of the dominant allele. In the case where the corresponding base on the antisense strand nucleotide sequence of the dominant allele is, for example, A (in this case, the original base in the nucleotide sequence in the sense strand of the dominant allele is T), the mismatch base is A, guanine (G), or cytosine (C), which cannot base-pair with A. In the case where the corresponding base on the antisense strand nucleotide sequence of the dominant allele is T (in this case, the original base in the nucleotide sequence in the sense strand of the dominant allele is A), the mismatch base is U or C, which cannot base-pair with T. In the case where the corresponding base on the antisense strand nucleotide sequence of the dominant allele is G (in this case, the original base in the nucleotide sequence in the sense strand of the dominant allele is C), the mismatch base is G or A, which cannot base-pair with G. In the case where the corresponding base on the antisense strand nucleotide sequence of the dominant allele is C (in this case, the original base in the nucleotide sequence in the sense strand of the dominant allele is G), the mismatch base is C, A, or U, which cannot base-pair with C.

The mismatch mutation is located at a predetermined position in the RNAi sense strand region. This predetermined position is any one base at the 3rd to 8th positions downstream from the standard mutation point (0th position), preferably, at the 3rd to 5th positions and the 7th to 8th positions downstream therefrom, more preferably at the 3rd to 5th positions downstream therefrom. In this regard, the mismatch base is not positioned at the 3' end of the RNAi sense strand region.

(Component of Double-Stranded RNAi Molecule)

Figure 3:
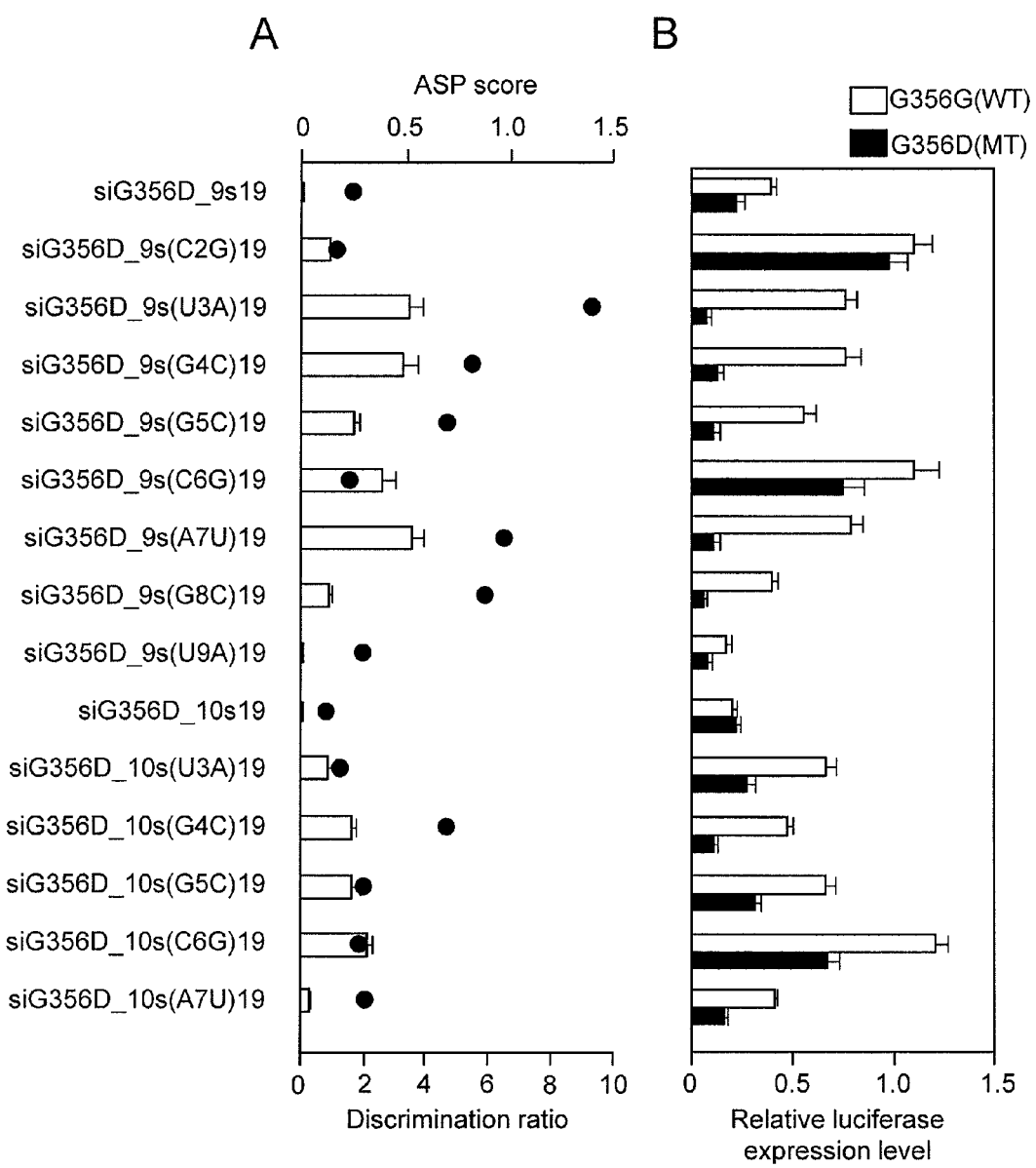
FIG. 3 shows the ASP-RNAi effect of ALK2-G356D-siRNA on mutant ALK2-G356D.

The double-stranded RNAi molecule, such as an siRNA, contained in the suppressing agent of the present aspect can further comprise, as shown in FIG. 1A, 3'-terminally added bases (0105) at the 3' end of each polynucleotide strand, in addition to the components RNAi sense strand region (0101), RNAi antisense strand region (0102), and mismatch base (0103) common to the RNAi molecules. The "3'-terminally added bases" (0105) are constituted of two bases: thymine-thymine (TT) or uracil-uracil (UU). The RNAi molecule having these added bases can enhance RNAi suppression efficiency (Tuschl T et al., 1999, Genes Dev, 13 (24): 3191-7).

(Component of Single-Stranded RNAi Molecule)

The single-stranded RNAi molecule, such as an shRNA, contained in the suppressing agent of the present aspect further comprise, as shown in FIG. 1B, a short spacer sequence (0106) that links the RNAi sense strand region (0101) and the RNAi antisense strand region (0102), in addition to the components RNAi sense strand region (0101), RNAi antisense strand region (0102), and mismatch base (0103) common to the RNAi molecules. The spacer sequence can be usually a 3- to 24-base, preferably 4- to 15-base arbitrary nucleotide sequence that does not self-pair. Thus, the single-stranded RNAi molecule consists of 35 bases (16×2+3) to 84 bases (30×2+24) as a whole. The RNAi sense strand region and the RNAi antisense strand region form base pairs with each other within the RNAi molecule, while the spacer sequence flanked thereby forms a loop structure. As a result, the whole molecule assumes a hairpin stem-loop structure. Upon introduction into a cell, the single-stranded RNAi molecule having this structure is processed into an siRNA duplex by the action of endonuclease called Dicer within the cytoplasm. The RNAi antisense strand region in the duplex is incorporated into an RNA-induced silencing complex (RISC), which can in turn suppress the post-transcriptional and pre-translational expression of the target gene through the same RNAi mechanism as in the double-stranded RNAi molecule.

1-4. Constitution of Expression Vector

In the present specification, the "expression vector" refers to a vector that serves as an active ingredient contained in the suppressing agent of the present aspect, wherein a DNA encoding the RNAi molecule is expressibly inserted in a vector for expression.

In the case of the expression vector of the present aspect for the double-stranded RNAi molecule such as an siRNA, DNA fragments encoding the RNAi sense strand region and the RNAi antisense strand region, respectively, may be inserted to two different vectors for expression or may be inserted as DNA fragments whose expressions are independently controlled, into one vector for expression. In the case of the expression vector of the present aspect for the single-stranded RNA molecule such as an shRNA, a DNA fragment encoding the single-stranded RNA molecule may be inserted to a predetermined position in a vector for expression.

In the present specification, the "vector for expression" refers to a backbone moiety in the expression vector of the present aspect, i.e., a moiety other than the DNA fragment encoding the RNAi molecule of the first aspect in the expression vector of the present aspect. The type of the vector for expression is not particularly limited and is preferably a plasmid or a virus. These vectors may be selected appropriately according to a host to be transfected. In the case where the host to be transfected is, for example, a human, an expression vector known in the art can be used, for example, a virus such as adenovirus, retrovirus, lentivirus, or adeno-associated virus, or a vector based on a non-viral vector. In the case where the host to be transfected is a plant, a plasmid such as a binary vector of pBI or pRI series, or a virus such as cauliflower mosaic virus (CaMV), bean golden mosaic virus (BGMV), or tobacco mosaic virus (TMV) can be used. Alternatively, in the case where the host to be transfected is *E. coli*, for example, a plasmid of pBI, pPZP, pSMA, pUC, pBR, or pBluescript series (Stratagene) can be used. In addition, various expression vectors for various types of hosts commercially available from each life science manufacturer may be used.

The vector for expression can contain a regulatory region such as a promoter, an enhancer, or a terminator, or a marker region such as a selective marker gene. Their respective types are not particularly limited. Those known in the art may be selected appropriately according to the host to be transfected with the expression vector.

Examples of the promoter that is operable in *E. coli* include: lac, trp, and tac promoters; and phage-derived T7, T3, SP6, PR, and PL promoters. Examples of the promoter that is operable in yeast include yeast glycolysis gene-derived promoters, alcohol dehydrogenase gene promoter, TPI1 promoter, and ADH2-4-c promoter. Examples of the promoter that is operable in plant cells include cauliflower mosaic virus (CaMV) 35S promoter, nopaline synthase gene promoter (Pnos), *Zea mays*-derived ubiquitin promoter, rice-derived actin promoter, and tobacco-derived PR protein promoter. Examples of the promoter that is operable in insect cells include polyhedrin promoter, P10 promoter, *Autographa californica* polyhedrosis basic protein promoter, baculovirus immediate early gene 1 promoter, and baculovirus 39K delayed-early gene promoter. RNA polymerase II (Pol II) promoter or RNA polymerase III (Pol III) promoter is preferably used as a promoter that is operable in animal cells including human cells. The promoter is preferably Pol III promoter, particularly preferably, for example, U6 or H1 promoter. Alternatively, a site-specific promoter that induces gene expression only at a particular site in vivo may be used for any of these hosts. In the case where DNA fragments encoding the RNAi sense strand region and the RNAi antisense strand region, respectively, are inserted into two different vectors for expression, promoters used in the vectors are preferably the same as each other or different promoters having equivalent expression activities so that both the RNA strands are expressed at equivalent levels.

1-5. Design and Production of RNAi Molecule

Figure 2:
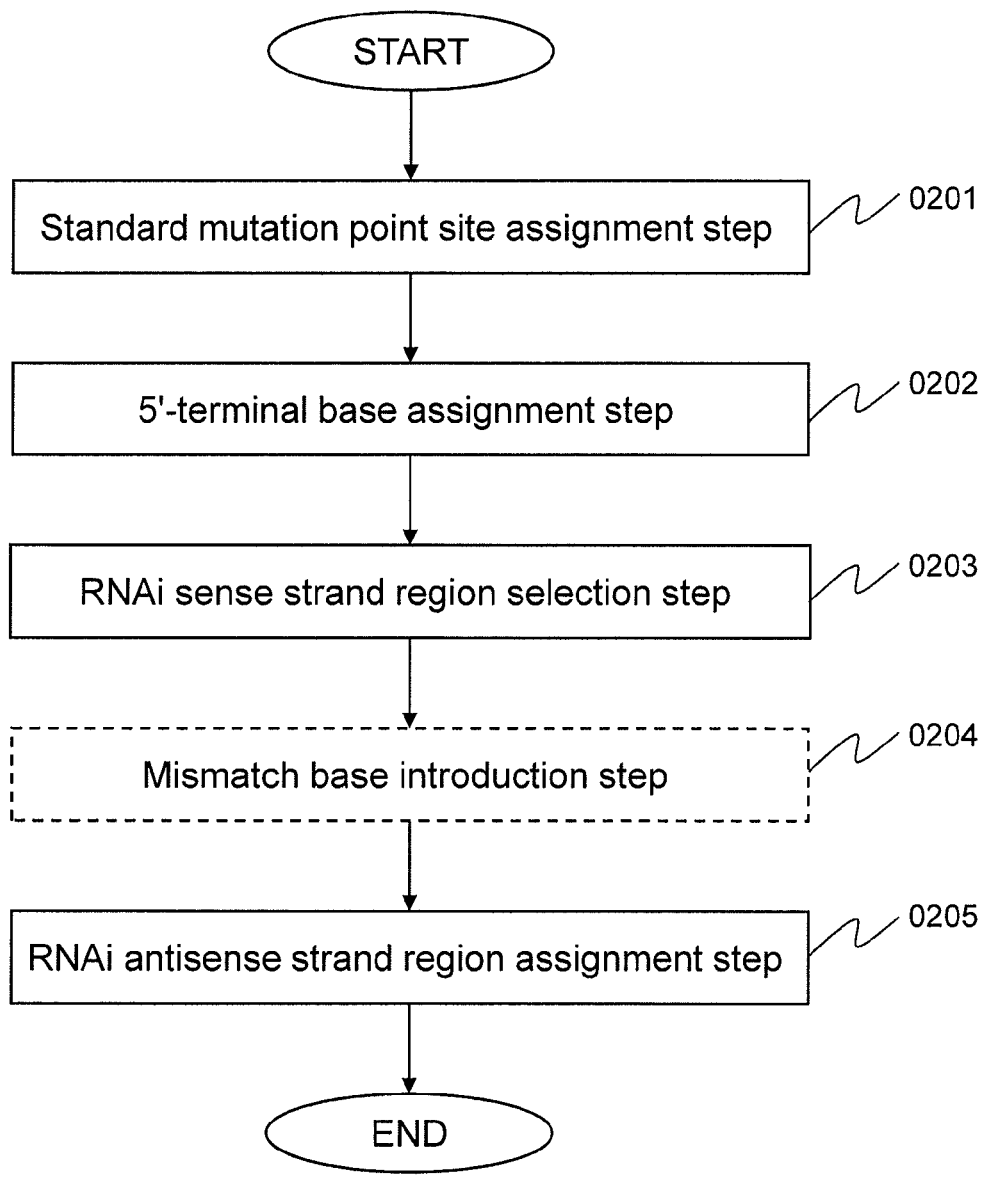
FIG. 2 shows a flow chart of a method for designing an RNAi molecule. A mismatch base introduction step (0204) represented by the broken line may be performed after any of a standard mutation point assignment step (0201), a 5'-terminal base assignment step (0202), and an RNAi sense strand region selection step (0203).

The method for designing the RNAi molecule contained in the suppressing agent of the present aspect will be described. This design method comprises, as shown in FIG. 2, a standard mutation point assignment step (0201), a 5'-terminal base assignment step (0202), an RNAi sense strand region selection step (0203), a mismatch base introduction step (0204), and an RNAi antisense strand region assignment step (0205). The standard mutation point assignment step, the 5'-terminal base assignment step, the RNAi sense strand region selection step, and the RNAi antisense strand region assignment step are performed in this order, whereas the mismatch base introduction step may be performed after any of the standard mutation point assignment step, the 5'-terminal base assignment step, and the RNAi sense strand region selection step. Hereinafter, each step will be described.

The "standard mutation point assignment step" (0201) is the step of assigning one dominant point mutation site present in the nucleotide sequence of the dominant allele of a target gene as a standard mutation point. In the case where the dominant point mutation site in the dominant allele is only one base, this base is assigned as a standard mutation point. Alternatively, in the case where the dominant allele contains two or more bases as dominant point mutation sites, any one of the bases can be selected as a standard mutation point. Preferably, the dominant point mutation site is selected so that a consequent GC content in the RNAi sense strand region is 20 to 80%, preferably 30 to 70%, more preferably 40 to 60%.

The "5'-terminal base assignment step" (0202) is the step of assigning a base at any of the 7th to 10th positions upstream from the standard mutation point in the nucleotide sequence of the dominant allele as the 5'-terminal base of the RNAi sense strand region. As described above, in the double-stranded RNAi molecule, the 5'-terminal base assigned in this step corresponds to the 5'-terminal base of the polynucleotide strand comprising the RNAi sense strand region. Alternatively, in the single-stranded RNAi molecule, the 5'-terminal base assigned in this step corresponds to the 5'-terminal base of this molecule. Thus, the end(s) at one side of the RNAi molecule is determined by this step.

The "RNAi sense strand region selection step" (0203) is the step selecting a downstream 16- to 30-base nucleotide sequence starting at the base assigned as the 5'-terminal base in the 5'-terminal base assignment step on the nucleotide sequence of the dominant allele, as an RNAi sense strand region from a nucleotide sequence in the sense strand of the dominant allele. By this step, a target region of the dominant allele by the RNAi molecule is determined. Preferably, the base corresponding to T in the nucleotide sequence (DNA sequence) of the dominant allele is substituted by U for the nucleotide sequence of the RNAi sense strand region.

The "mismatch base introduction step" (0204) is the step of introducing a mismatch base to within the selected RNAi sense strand region. One base at the 3rd to 8th positions downstream from the standard mutation point is selected and substituted by a base different from the corresponding one in the nucleotide sequence in the sense strand of the dominant allele, thereby introducing the mismatch base therein. The mismatch base is preferably a base at any of the 3rd to 5th positions and the 7th to 8th positions downstream therefrom, more preferably a base at any of the 3rd to 5th positions downstream therefrom. It should be noted that the base is selected so that the base after substitution cannot base-pair with the corresponding base in the antisense strand nucleotide sequence of the dominant allele. Provided that the corresponding base in the antisense strand of the dominant allele is, for example, A, A, G, or C may be used. Provided that the corresponding base in the antisense strand of the dominant allele is T, U or C may be used. Provided that the corresponding base in the antisense strand of the dominant allele is G, G or A may be used. Provided that the corresponding base in the antisense strand of the dominant allele is C, C, U, or A may be used.

The "RNAi antisense strand region assignment step" (0205) is the step of assigning a nucleotide sequence complementary to the nucleotide sequence of the selected RNAi sense strand region as an RNAi antisense strand region. As a result, the basic structure of the double-stranded RNAi molecule is determined.

The steps described above are common to both the single-stranded and double-stranded RNAi molecules that can be contained in the suppressing agent of the present aspect. Next, a 3'-terminal addition step and a spacer linking step unique to the double-stranded and single-stranded RNAi molecules, respectively, will be described.

The "3'-terminal addition step" is an optional step unique to the double-stranded RNAi molecule. A feature of this step is that thymine-thymine (TT) or uracil-uracil (UU) is added to each of the 3' ends of the RNAi sense strand region and the RNAi antisense strand region thus designed.

The "spacer linking step" is an essential step unique to the single-stranded RNAi molecule. This step is the step of linking the 3' end of the RNAi sense strand region thus designed to the 5' end of the RNAi antisense strand region via the 5' and 3' ends, respectively, of a spacer sequence to form a single-stranded molecule. The spacer sequence may be an arbitrary nucleotide sequence consisting of 3 to 24 bases, preferably 4 to 15 bases. Preferably, the nucleotide sequence does not form a base pair within the spacer sequence.

The RNAi molecule of the present aspect can be synthesized by a chemical synthesis method based on the nucleotide sequence designed by the method described above. The chemical synthesis of the RNAi molecule may employ a contract manufacturing service provided by each life science manufacturer (e.g., Sigma-Aldrich Corp., Bex Co., Ltd., Takara Bio Inc., and Invitrogen Corp.).

Alternatively, the nucleotide sequence designed by the method described above is temporarily converted to a DNA sequence, and DNA chemically synthesized on the basis of the sequence can be subjected to cloning and then to an in vitro RNA transcription method known in the art to prepare the RNAi molecule of the present aspect as RNA. For the in vitro RNA transcription method, see, for example, Sambrook, J. et. al., (1989) Molecular Cloning: A Laboratory Manual Second Ed., Cold Spring Harbor Laboratory Press, Cold Spring Harbor, N.Y. Alternatively the method of Ui-Tei et al. (Nucleic Acids Res., 32: 936-948, 2004), the method of Reynolds et al. (Nat. Biotechnol., 22: 326-330, 2004), or the method of Amarzguioui et al. (Biochem. Biophys. Res. Commun., 316: 1050-1058, 2004) can be referred to.

1-6. Preparation of Expression Vector

The expression vector contained in the suppressing agent of the present aspect can be prepared basically according to a method known in the art, for example, a method described in Sambrook, J. et. al., (1989) Molecular Cloning: a Laboratory Manual Second Ed., Cold Spring Harbor Laboratory Press, Cold Spring Harbor, N.Y.

As a specific example, first, the nucleotide sequence of the RNAi molecule is determined according to the method described in the preceding paragraph "1-5. Design and production of RNAi molecule". Subsequently, a sense strand DNA and an antisense strand DNA are each synthesized by a chemical synthesis method or the like on the basis of a DNA sequence corresponding thereto. In this procedure, preferably, appropriate restriction sites are added to both ends of each strand, or the strands are modified so that appropriate cohesive ends occur after annealing. DNA synthesis may employ a contract manufacturing service provided by each life science manufacturer. Both the strands thus synthesized are mixed for annealing to prepare a double-stranded DNA fragment. Then, the restriction sites, if present at the ends, are cleaved, if necessary, with restriction enzymes appropriate therefor. The 5' end of each strand is further phosphorylated, if necessary, with T4 polynucleotide kinase or the like. Subsequently, the double-stranded DNA fragment thus prepared is linked to the corresponding restriction sites downstream of a promoter in a vector for expression. Alternatively, the DNA fragment is temporarily linked and cloned into a cloning vector, and then, a fragment cleaved therefrom may be linked to a vector for expression.

1-7. Effect

According to the agent for suppressing the expression of a dominant allele according to the present aspect, the RNAi molecule serving as an active ingredient can selectively and efficiently suppress the expression of the target allele with substantially no or little influence on the expression of a non-target allele, even if these alleles differ in their nucleotide sequences only by one base.

When the suppressing agent of the present aspect is introduced into a cell, the RNAi molecule serving as an active ingredient can directly act on the targeted dominant allele or the RNAi molecule encoded by the DNA contained in the expression vector serving as an active ingredient can act after its expression on the targeted dominant allele, thereby suppressing the expression of the dominant allele by the silencing mechanism of RNAi. Thus, the suppressing agent comprising the RNAi molecule can confer its ASP-RNAi effect on the recipient cell or the like in a short time. By contrast, the suppressing agent comprising the expression vector can continuously confer its ASP-RNAi effect as long as the expression vector is maintained in the cell after administration. Hence, combined use thereof can effectively suppress the expression of the dominant allele.

A pharmaceutical composition (described later) supplemented with the suppressing agent of the present aspect can treat or relieve various diseases caused by dominant alleles, which have previously been difficult to treat, and can also be used in the improvement of animal or plant species, etc.

2. Pharmaceutical Composition

The second aspect of the present invention relates to a pharmaceutical composition comprising the suppressing agent of the first aspect.

2-1. Constitution

The pharmaceutical composition of the present invention comprises the RNAi molecule and/or the expression vector as an active ingredient in a vehicle. Examples of the vehicle include solvents such as water, ethanol, propylene glycol, ethoxylated isostearyl alcohol, polyoxylated isostearyl alcohol, and polyoxyethylene sorbitan fatty acid esters. Preferably, such a vehicle is sterilized and adjusted, if necessary, to be isotonic with blood.

The content of the RNAi molecule and/or expression vector as an active ingredient in the pharmaceutical composition of the present invention differs depending on various conditions such as the type of a causative gene of a disease to be treated, the mechanism of onset thereof on which the gene acts, the functions or effects and stability of the RNAi molecule, the expression level of the expression vector, the dosage form of the pharmaceutical composition, the type of the carrier used, an administration method, and the state of a test subject receiving the pharmaceutical composition. This content may be selected appropriately on the basis of a technique known in the art. Specifically, for example, the content of the RNAi molecule or the expression vector of the present invention in an injection solution to be administered to an adult human male (body weight: 60 kg) that does not require combined use with another pharmaceutical drug can be approximately 0.01% (w/v) to approximately 20% (w/v), preferably approximately 0.1% (w/v) to approximately 10% (w/v), per dosage unit of the injection solution. Specifically, for example, 1 ml of one injection can usually contain 1 μg to 200 μg of the siRNA. When the nucleic acid of the present invention needs to be administered in large amounts for obtaining the pharmacological effect of the pharmaceutical composition of the present invention, the pharmaceutical composition may be administered at several divided doses in order to reduce burdens on the test subject.

The pharmaceutical composition of the present invention may further comprise a pharmaceutically acceptable carrier, if necessary. The "pharmaceutically acceptable carrier" refers to an additive usually used in the pharmaceutical formulating art. Examples thereof include excipients, binders, disintegrants, fillers, emulsifiers, glidants or flow aids, and lubricants.

Examples of the excipients include sugars such as monosaccharides, disaccharides, cyclodextrin, and polysaccharides (more specifically including, but not limited to, glucose, sucrose, lactose, raffinose, mannitol, sorbitol, inositol, dextrin, maltodextrin, starch, and cellulose), metal salts (e.g., sodium chloride, sodium phosphate or calcium phosphate, calcium sulfate, magnesium sulfate, and calcium carbonate), citric acid, tartaric acid, glycine, low-, middle-, or high-molecular weight polyethylene glycol (PEG), Pluronic, kaolin, silicic acid, and combinations thereof.

Examples of the binders include starch glues composed of corn, wheat, rice, or potato starch, simple syrup, glucose solution, gelatin, tragacanth, methylcellulose, hydroxypropylmethylcellulose, sodium carboxymethylcellulose, shellac, and/or polyvinylpyrrolidone.

Examples of the disintegrants include the starches described above, lactose, carboxymethyl starch, cross-linked polyvinylpyrrolidone, agar, laminaran powder, sodium bicarbonate, calcium carbonate, alginic acid or sodium alginate, polyoxyethylene sorbitan fatty acid ester, sodium lauryl sulfate, monoglyceride stearate, and salts thereof.

Examples of the fillers include the sugars described above, and/or calcium phosphate (e.g., tricalcium phosphate or calcium hydrogen phosphate).

Examples of the emulsifiers include sorbitan fatty acid ester, glycerin fatty acid ester, sucrose fatty acid ester, and propylene glycol fatty acid ester.

Examples of the glidants or flow aids and the lubricants include silicate, talc, stearate, and polyethylene glycol.

These carriers are used mainly for facilitating the formulation of the dosage form and maintaining the dosage form and the drug effects and may be used appropriately according to the need. The pharmaceutical composition may also comprise, in addition to the additives described above, optional additives such as corrigents, solubilizers, suspending agents, diluents, surfactants, stabilizers, absorption promoters, expanders, wetting agents, humectants, adsorbents, disintegration inhibitors, coating agents, coloring agents, preservatives, antioxidants, fragrances, flavors, sweeteners, and buffers.

The pharmaceutical composition of the present invention can also contain another drug without losing the pharmacological effect of the RNAi molecule. For example, an injection may contain a predetermined amount of an antibiotic.

The pharmaceutical composition of the present aspect can be prepared as a so-called combination formulation further containing another pharmaceutically acceptable active ingredient without deactivating the RNAi molecule and/or the expression vector in the suppressing agent of the first aspect.

The dosage form of the pharmaceutical composition of the present aspect is not particularly limited as long as the form does not deactivate the RNAi molecule or the expression vector as an active ingredient in the suppressing agent or the additional active ingredient. For example, any of liquid, solid, and semisolid forms may be used. Specific examples of the dosage form include: parenteral dosage forms such as injections, suspensions, emulsions, eye drops, nasal drops, creams, ointments, plasters, patches, and suppositories; and oral dosage forms such as solutions, powders, granules, tablets, capsules, sublingual formulations, and troches. The dosage form of the pharmaceutical composition of the present aspect comprising the suppressing agent comprising the RNAi molecule or the expression vector as an active ingredient is preferably an injection.

2-2. Administration Method

The pharmaceutical composition of the present aspect can be administered to an organism in a pharmaceutically effective amount for the treatment of the disease of interest. The organism as a recipient is a vertebrate, preferably a mammal, more preferably a human.

In the present specification, the "pharmaceutically effective amount" refers to a dose required, for the RNAi molecule and/or the expression vector as an active ingredient in the suppressing agent contained in the pharmaceutical composition of the present invention, to treat the disease of interest or relieve its symptoms (specifically, a dose at which the active ingredient can suppress the trait exhibition of the dominant allele responsible for the disease) with no or little adverse reaction (e.g., suppression of the expression of wild-type alleles) harmful to the recipient organism. The specific amount differs depending on the type of the targeted gene, the position of the dominant point mutation in the dominant allele, the trait-exhibiting effect of the dominant allele, the dosage form used, information about a test subject (or a human subject), and an administration route. The range of the pharmaceutically effective amount and a preferable administration route for administration to a human are generally set on the basis of data obtained from cell culture assay and animal experiments. The dose is finally determined and adjusted at a physician's discretion according to an individual human subject. In this case, information about the human subject to be considered includes, for example, the degree of progression or severity of the disease, general health conditions, age, body weight, sex, diet, drug sensitivity, and resistance to treatment.

The RNAi molecule of the present invention may be administered systemically or locally. An appropriate route can be selected according to, for example, the type, site of onset, degree of progression of the disease. For a disease whose onset is localized at a site, local administration is preferable, in which the RNAi molecule of the present invention is directly administered to the site of onset and its neighborhood through injection or the like. This is because the RNAi molecule of the present invention can be delivered in sufficient amounts to the site (tissue or organ) to be treated with little influence on the other tissues. For a disease, such as metastatic cancer, whose site to be treated cannot be identified or a disease whose onset is systemic, systemic administration through intravenous injection or the like is preferable, though the administration route is not limited thereto. This is because the RNAi molecule of the present invention can be distributed throughout the body via blood flow and thereby delivered even to a lesion that cannot be found by diagnosis.

The RNAi molecule of the present invention can be administered by any appropriate method without deactivating the active ingredient contained. For example, any of parenteral (e.g., injection, aerosol, application, eye drop, and nasal drop) and oral administrations can be performed. Injection is preferable.

In the case of administration through injection, an injection site is not particularly limited. The injection site may be any site at which the RNAi molecule of the present invention or the RNAi molecule produced from the expression vector of the present invention can exert its functions on the target molecule and achieve the purpose of the pharmaceutical composition. Examples thereof include intravenous, intraarterial, intrahepatic, intramuscular, intraarticular, intramedullary, intraspinal, intraventricular, transdermal, hypodermic, intradermal, intraperitoneal, intranasal, enteral, and sublingual injections. Intravascular injection such as intravenous injection or intraarterial injection is preferable. This is because, as described above, the pharmaceutical composition of the present invention can be distributed throughout the body via blood flow and also because this injection is relatively low invasive.

2-3. Use

The pharmaceutical composition of the present invention can be used for the treatment of a disease. The pharmaceutical composition of the present invention can be applied to a disease caused by the expression of a dominant allele, for example, an autosomal dominantly inherited disease, thereby selectively suppressing the expression of the dominant allele while allowing a trait to be manifested from the other allele (e.g., wild-type allele encoding a protein having normal functions). Thus, the pharmaceutical composition of the present invention can be used in the treatment of inherited diseases, cancers, and the like, which have previously been difficult to treat, and can also be used in the improvement of animal or plant species, etc. In this regard, the disease targeted by the pharmaceutical composition of the present aspect is a disease based on a dominant trait brought about by a dominant allele targeted by the RNAi molecule contained in the suppressing agent or the RNAi molecule expressed from the expression vector contained therein. Specific examples of such diseases include: autosomal dominantly inherited diseases in humans, such as Huntington's disease, fibrodysplasia ossificans progressiva (FOP), familial amyloid polyneuropathy, familial hypercholesterolemia, maturity-onset diabetes of the young (MODY), Marfan's syndrome, autosomal dominant progressive muscular dystrophy, autosomal dominant osteogenesis imperfecta, autosomal dominant retinitis pigmentosa, autosomal dominant congenital cataract, nodular sclerosis, hereditary palmoplantar keratoderma, familial polyposis coli, autosomal dominant polycystic kidney disease, retinoblastoma, and neurofibroma; and malignant neoplasms such as non-small cell lung cancer (NSCLC), pancreatic cancer, large intestine cancer, and medullary thyroid cancer. Hence, the pharmaceutical composition of the present aspect can be applied to various diseases by using an RNAi molecule against a dominant allele causative of a disease to be treated or an expression vector comprising a DNA encoding it as an active ingredient.

EXAMPLES

Example 1

Test on Asp-RNAi Effect of siRNA Against ALK2 Gene

An siRNA (ALK2-siRNA) against ALK2 gene, the causative gene of fibrodysplasia ossificans progressiva (FOP) known as an autosomal dominantly inherited disease in humans, was designed and tested for its ASP-RNAi effect on each of a dominant allele and a wild-type allele.

(1) Design and Preparation of ALK2-siRNA

Each FOP patient has a point mutation that substitutes the 617th base G (counted from A in the start codon as the first position; the same holds true for the description below) in human ALK2 gene (Accession No. NM_001105) by A (R206H amino acid mutation: lysine at the 206th position counted from initiating methionine is substituted by histidine) or substitutes the 1067th base G by A (G356D amino acid mutation: glycine 356 is substituted by aspartic acid). Thus, various ALK2-siRNAs were designed with each point mutation assigned as a standard mutation point according to the method for designing the RNAi molecule described in the first aspect. Table 1 shows the nucleotide sequences of sense and antisense strands of ALK2-siRNAs designed with the point mutation at the 617th position (R206H amino acid mutation) as a standard mutation point. Table 2 shows the nucleotide sequences of sense and antisense strands of ALK2-siRNAs designed with the point mutation at the 1067th position (G356D amino acid mutation) as a standard mutation point. In this regard, nucleotide sequences are shown in each table except for their 3'-terminal UU overhang sequences in sense and antisense strands for the sake of convenience.

TABLE 1

| siRNA name | sense/ antisense | Nucleotide sequence (5' → 3') | SEQ ID NO: |
|---|---|---|---|
| siR206H_8s19 | ss | AGUGGCUCACCAGAUUACA | 1 |
|  | as | UGUAAUCUGGUGAGCCACU | 2 |
| siR206H_8s(G4C)19 | ss | AGUGGCUCACCACAUUACA | 3 |
|  | as | UGUAAUCUGGUGAGCCACU | 4 |
| siR206H_8s(A5U)19 | ss | AGUGGCUCACCAGUUUACA | 5 |
|  | as | UGUAAACUGGUGAGCCACU | 6 |
| siR206H_8s(A5G)19 | ss | AGUGGCUCACCAGGUUACA | 7 |
|  | as | UGUAACCUGGUGAGCCACU | 8 |
| siR206H_8s(A5C)19 | ss | AGUGGCUCACCAGCUUACA | 9 |
|  | as | UGUAAGCUGGUGAGCCACU | 10 |
| siR206H_7s(A5U)18 | ss | GUGGCUCACCAGUUUACA | 11 |
|  | as | UGUAAACUGGUGAGCCAC | 12 |
| siR206H_7s(A5U)19 | ss | GUGGCUCACCAGUUUACAC | 13 |
|  | as | GUGUAAACUGGUGAGCCAC | 14 |
| siR206H_9s19 | ss | CAGUGGCUCACCAGAUUAC | 89 |
|  | as | GUAAUCUGGUGAGCCACUG | 90 |
| siR206H_9s(A3U)19 | ss | CAGUGGCUCACCUGAUUAC | 91 |
|  | as | GUAAUCAGGUGAGCCACUG | 92 |

TABLE 2

| siRNA name | sense/ anti-sense | Nucleotide sequence (5' → 3') | SEQ ID NO: |
|---|---|---|---|
| siG356D_9s19 | ss | CAGAUUUGGACCUGGCAGU | 15 |
|  | as | ACUGCCAGGUCCAAAUCUG | 16 |
| siG356D_9s(C2G)19 | ss | CAGAUUUGGACGUGGCAGU | 17 |
|  | as | ACUGCCACGUCCAAAUCUG | 18 |
| siG356D_9s(U3A)19 | ss | CAGAUUUGGACCAGGCAGU | 19 |
|  | as | ACUGCCUGGUCCAAAUCUG | 20 |
| siG356D_9s(G4C)19 | ss | CAGAUUUGGACCUCGCAGU | 21 |
|  | as | ACUGCGAGGUCCAAAUCUG | 22 |
| siG356D_9s(G5C)19 | ss | CAGAUUUGGACCUGCCAGU | 23 |
|  | as | ACUGGCAGGUCCAAAUCUG | 24 |
| siG356D_9s(C6G)19 | ss | CAGAUUUGGACCUGGGAGU | 25 |
|  | as | ACUCCCAGGUCCAAAUCUG | 26 |
| siG356D_9s(A7U)19 | ss | CAGAUUUGGACCUGGCUGU | 27 |
|  | as | ACAGCCAGGUCCAAAUCUG | 28 |
| siG3560_9s(G8C)19 | ss | CAGAUUUGGACCUGGCACU | 29 |
|  | as | AGUGCCAGGUCCAAAUCUG | 30 |
| siG356D_9s(U9A)19 | ss | CAGAUUUGGACCUGGCAGA | 31 |
|  | as | UCUGCCAGGUCCAAAUCUG | 32 |

TABLE 2-continued

| siRNA name | sense/anti-sense | Nucleotide sequence (5' → 3') | SEQ ID NO: |
|---|---|---|---|
| siG356D_10s19 | ss | GCAGAUUUGGACCUGGCAG | 33 |
| | as | CUGCCAGGUCCAAAUCUGC | 34 |
| siG356D_10s(U3A)19 | ss | GCAGAUUUGGACCAGGCAG | 35 |
| | as | CUGCCUGGUCCAAAUCUGC | 36 |
| siG356D_10s(G4C)19 | ss | GCAGAUUUGGACCUCGCAG | 37 |
| | as | CUGCGAGGUCCAAAUCUGC | 38 |
| siG356D_10s(G5C)19 | ss | GCAGAUUUGGACCUGCCAG | 39 |
| | as | CUGGCAGGUCCAAAUCUGC | 40 |
| siG356D_10s(C6G)19 | ss | GCAGAUUUGGACCUGGGAG | 41 |
| | as | CUCCCAGGUCCAAAUCUGC | 42 |
| siG356D_10s(A7U)19 | ss | GCAGAUUUGGACCUGGCUG | 43 |
| | as | CAGCCAGGUCCAAAUCUGC | 44 |

In each table, the siRNA name was designated as follows: taking "siR206H_8s(A5U)19-ss" as an example, "siR206H" represents an siRNA containing the standard mutation point at the 617th position that causes the R206H amino acid substitution; "8s" represents the presence of 8 bases (8 nucleotides) upstream of the standard mutation point; the symbol within the parenthesis, such as "(A5U)", represents a mismatch base and means that A was substituted by U at the 5th position downstream from the standard mutation point; and the subsequent number "19" means the total number of bases (total number of nucleotides) in the siRNA; and the final symbol "ss" represents the sense strand sequence of the siRNA. Likewise, the final symbol "as" represents the antisense strand sequence of the siRNA. The siRNA without parenthesis means the absence of a mismatch base.

For the sense strand nucleotide sequences in each table, the standard mutation points are indicated by boldface, while the mismatch bases are indicated by underlined characters.

On the basis of the nucleotide sequences of Tables 1 and 2, each siRNA was chemically synthesized. The synthesis was entrusted to Sigma-Aldrich Corp. The synthesized siRNA having the annealed pair of sense and antisense strands was used in the experiment.

(2) Construction of Reporter Allele Expression Plasmid

In order to evaluate the ASP-RNAi effects of the ALK2-siRNAs prepared in the preceding paragraph (1) and select suitable ALK2-siRNAs, pGL3-TK plasmids (Ohnishi et al., 2005) expressing *Photinus* luciferase gene and phRL-TK plasmids (Promega Corp.) expressing *Renilla* luciferase gene were used to construct expression plasmids for dominant mutants targeted by siRNAs and non-target normal reporter alleles.

The methods for designing a synthetic oligo DNA corresponding to each dominant allele containing a dominant point mutation site, inserting the DNA into a reporter plasmid, and selecting suitable siRNAs followed Non Patent Literature 6. Specifically, 39-base oligo DNA sense and antisense strands each containing a dominant point mutation site at the 617th or 1097th position of the ALK2 gene responsible for FOP were synthesized (by Sigma-Aldrich Corp.). Similarly, an oligo DNA was synthesized against the point mutation-free normal allele. Their specific nucleotide sequences are shown in Table 3. These sense and antisense strands contained linker sequences constituting restriction enzyme cleavage sites, at both ends of the sense and antisense strands of the ALK2 gene fragment. In the table, the standard mutation points (or bases at the corresponding positions for wild-type) are indicated by boldface, and the linker sequences are underlined.

TABLE 3

| Sequence name | sense/antisense | Nucleotide sequence (5' → 3') | SEQ ID NO: |
|---|---|---|---|
| R206H(MT) | ss | CTAGCATGCAAGAACAGTGGCTCACCAGATTACACTGTA | 45 |
| | as | GGCCTACAGTGTAATCTGGTGAGCCACTGTTCTTGCATG | 46 |
| R206R(WT) | ss | CTAGCATGCAAGAACAGTGGCTCGCCAGATTACACTGTA | 47 |
| | as | GGCCTACAGTGTAATCTGGCGAGCCACTGTTCTTGCATG | 48 |
| G356D(MT) | ss | CTAGCATGCGCATAGCAGATTTGGACCTGGCAGTCATGA | 49 |
| | as | GGCCTCATGACTGCCAGGTCCAAATCTGCTATGCGCATG | 50 |
| G356G(WT) | ss | CTAGCATGCGCATAGCAGATTTGGGCCTGGCAGTCATGA | 51 |
| | as | GGCCTCATGACTGCCAGGCCCAAATCTGCTATGCGCATG | 52 |

Next, the synthesized oligo DNA strands were annealed. Specifically, single-stranded oligo DNA sense and antisense strands (final concentration: 1 µM each), 10×annealing buffer (Invitrogen Corp.; final concentration: 1×), and sterilized water were mixed into a final volume of 10 µL, heat-treated at 80° C. for 5 minutes, and then left at room temperature for 30 minutes to form a duplex.

Subsequently, the oligo DNA duplex was inserted to two plasmids (described above) treated with restriction enzymes. Specifically, the pGL3-TK and phRL-TK plasmids were treated with restriction enzymes XbaI and NotI. Then, the oligo DNA duplex against the normal allele was inserted into the 3' untranslated region (3' UTR) of the reporter gene in the pGL3-TK plasmid, while the oligo DNA duplex against the dominant mutant allele was inserted into this region in the phRL-TK plasmid to construct normal ALK2 reporter allele expression plasmids and dominant mutant ALK2 reporter allele expression plasmids. Also, reporter allele expression plasmids were constructed in the same way as above except that the reporter genes were interchanged between the normal and dominant mutant alleles.

(3) Cell Culture

Human-derived cell line HeLa cells were cultured at 37° C. under 5% $CO_2$ using a DMEM culture solution (Wako Pure Chemical Industries, Ltd.) containing 10% fetal bovine serum (FBS; Invitrogen Corp.) and antibiotics (100 units/mL penicillin and 100 µg/mL streptomycin; Wako Pure Chemical Industries, Ltd.).

(4) Transfection and Reporter Assay

On the day before gene transfer, the HeLa cells were dispersed by trypsin digestion. The cell dispersion was then adjusted to a cell density of $1\times10^5$ cells/cm$^2$, inoculated to a 96-well culture plate, and cultured in an antibiotic-free DMEM culture solution. 24 hours later, the HeLa cells were cotransfected with each of 3 types of plasmids, i.e., (a) a pGL3-TK backbone plasmid (60 ng/well), which was the normal ALK2 reporter allele expression plasmid, (b) each phRL-TK backbone plasmid (20 ng/well), which was the mutant ALK2 dominant reporter allele expression plasmid, and (c) a pSV-β-galactosidase control plasmid (Promega Corp.) (10 ng/well), which was a β-galactosidase gene expression plasmid insusceptible to gene silencing by RNAi as an internal control, and various ALK2-siRNAs (shown in Table 1 or 2; final concentration: 20 nM) designed against the target ALK2 dominant mutant alleles. The negative control used was an siRNA (final concentration: 20 nM) that did not induce RNAi (siControl; Qiagen). The transfection of these nucleic acids employed Lipofectamine 2000 (Invitrogen Corp.). The transfection method followed the protocol included in the product. 24 hours after the nucleic acid transfer, cell extracts were prepared using (Dual-Luciferase reporter assay system) Passive lysis buffer included in the kit Dual-Luciferase reporter assay system (Promega Corp.). The respective activities of each expressed reporter allele (and two luciferases) and the control β-galactosidase were determined using Dual-Luciferase reporter assay system (Promega Corp.) and Beta-Glo assay system (Promega Corp.). The assay employed Fusion Universal Microplate Analyzer (Perkin Elmer Inc.). In order to further exclude measurement errors attributed to the difference in the activities of the two luciferases used as reporters, an experiment was also conducted using reporter genes interchanged between the mutation sites (R206H and G356D).

(5) Results

Various ALK2-siRNAs designed against each mutation site (R206H and G356D) in ALK2 were studied for their ASP-RNAi effects and the general structural rule of RNAi molecules suitable for ASP-RNAi induction by reporter assay using the reporter allele expression plasmids.

The expression suppressive effect of each siRNA was evaluated according to a discrimination ratio and an ASP score calculated on the basis of respective reporter luciferase activities derived from wild-type ALK2 and mutant ALK2.

In this context, the "discrimination ratio" (DR) refers to the relative expression ratio of the normal allele to the mutant allele obtained from the formula DR=(Normal allele expression level)/(Variant allele expression level). The larger value of the discrimination ratio means that the siRNA is more capable of discriminating between the normal allele and the mutant allele.

Also, the "ASP score" (allele-specificity score) is an evaluation method devised by the present inventors, and this value is obtained according to the formula shown below. The ASP score reflects both "specificity" for the mutant allele and "suppressive effect" thereon.

ASP score=[(Normal allele expression level)−(Variant allele expression level)]×(Normal allele expression level)

The formula reflects the degree of suppressive effect of the RNAi molecule on the mutant allele as "difference" from the expression level of the normal allele. This difference is further multiplied by the "normal allele expression level" to take into consideration nonspecific influence on the normal allele. The evaluation method based on the discrimination ratio, albeit useful, cannot take into consideration the influence of nonspecific suppression on the normal allele, in other words, the adverse reaction of RNAi against the normal allele, which is an important factor for ASP-RNAi. The ASP score, however, allows evaluation reflecting both "specificity" for the mutant allele and "suppressive effect" thereon. For example, even an siRNA capable of specifically discriminating between wild-type and mutant alleles with a high discrimination ratio produces a low ASP score when suppressing the expression of the wild-type allele more than a little.

Figure 4:
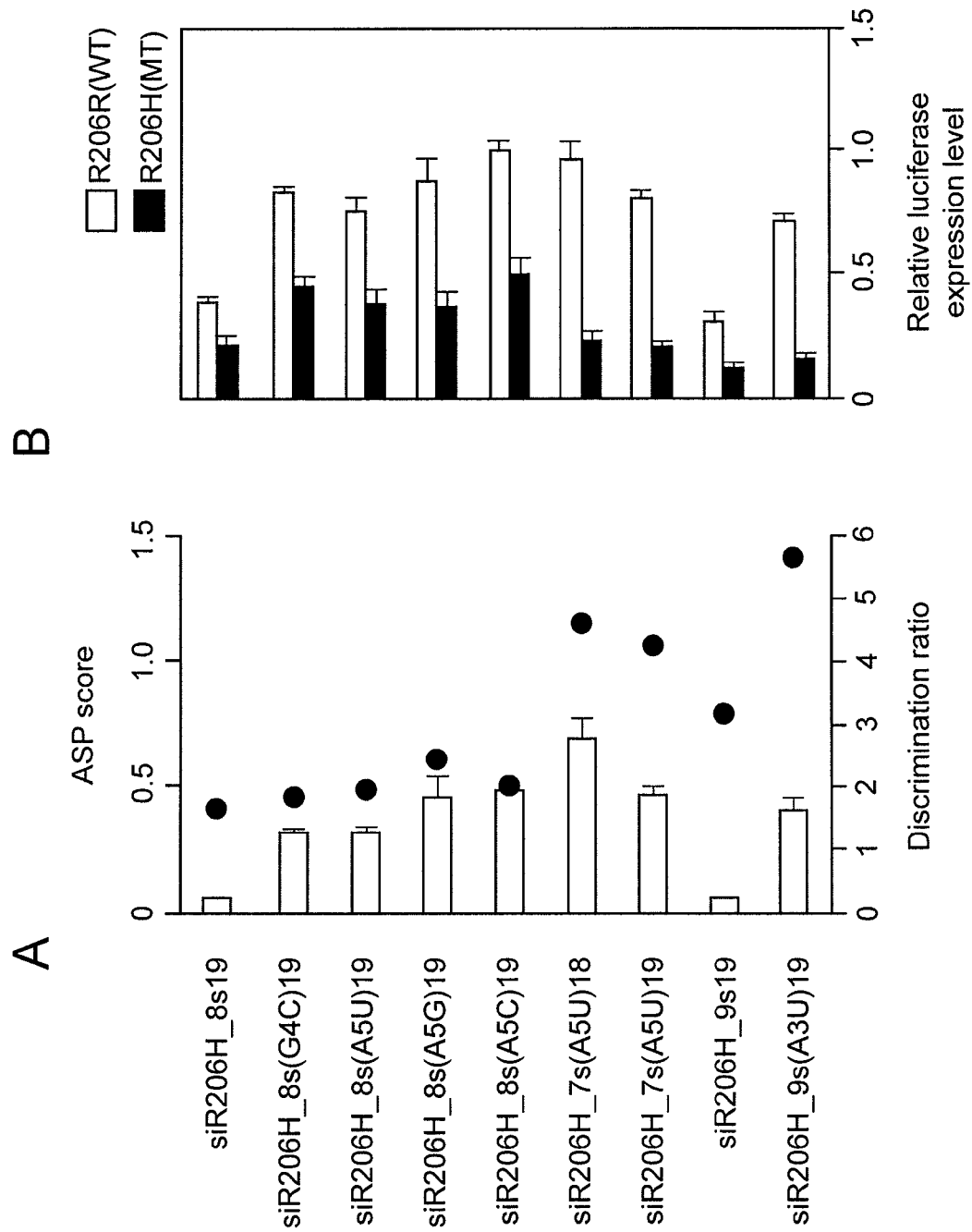
FIG. 4 shows the ASP-RNAi effect of ALK2-R206H-siRNA on mutant ALK2-R206H.

The results are shown in FIGS. 3 and 4. FIG. 3 shows the results of RNAi using ALK2-G356D-siRNA, and FIG. 4 shows the results of RNAi using ALK2-R206H-siRNA. FIGS. 3A and 4A show the discrimination ratio (plot) and ASP score (bar graph) of each siRNA used. FIGS. 3B and 4B show the relative expression levels of the non-target wild-type ALK2 sequence (WT-ALK2) and the target mutant ALK2 sequence (MT-ALK2) calculated on the basis of luciferase activity.

In FIG. 3, the control siG356D_9s19 targeted the ALK2-G356D mutation and consisted of mismatch base-free 19 bases in full length with 9 nucleotides upstream from the standard mutation point. The position of the mismatch base in this control was displaced one by one to test the optimum position for ASP-RNAi. siG356D_9s19 had a discrimination ratio of 1.64 and an ASP score of 0.02. This result indicates that siG356D_9s19 is less capable of discriminating between the wild-type and mutant alleles and strongly suppresses both the expressions of the wild-type and mutant alleles. Regarding siG356D_9s(C2G)19 to siG356D_9s(U9A)19 containing mismatch bases at the 2nd to 9th positions, respectively, downstream from the standard mutation point, siG356D_9s (U3A)19 to siG356D_9s(C8G)19 containing mismatch bases at the 3rd to 8th positions, respectively, had a very high discrimination ratio and ASP score, compared with the control siG356D_9s19. These results indicate that the siRNA having a mismatch at any of the 3rd to 8th positions downstream from the standard mutation point is highly capable of discriminating between the wild-type and mutant alleles and strongly suppresses the expression of the mutant allele while being hardly or much less able to suppress the expression level of the wild-type allele. This means that this siRNA is very useful with a high ASP-RNAi effect. This result suggested that the suitable position of the mismatch base is the 3rd to 8th positions downstream from the standard mutation point.

In order to confirm the generality of the results described above, 19-base (full length) siG356D_10s19 having 10 nucleotides upstream from the standard mutation point was used as a control to prepare siG356D_10s(U3A)19 to siG356D_10s(A7U)19 containing mismatch bases at the positions found effective for siG356D_9s19 (i.e., at the 3rd to 7th positions downstream from the standard mutation point), respectively. These siRNAs were tested for their ASP-RNAi effects. As a result, the control siG356D 10s19 had a discrimination ratio of 1.0 and an ASP score of 0.00, which were substantially equivalent to siG356D_9s19, whereas all the mismatch base-containing siRNAs produced a high discrimination ratio and ASP score compared with the control.

FIG. 4 shows the results about the control siR206H_8s19 targeting the ALK2-R206H mutation and the siRNAs containing mismatch bases at the positions confirmed to exert the ASP-RNAi effect of siG356D_9s19 (here, at the 4th and 5th positions downstream from the standard mutation point), respectively. The siRNA against the ALK2 R206H mutation containing a mismatch at the 4th or 5th position from the standard mutation point produced a high discrimination ratio and ASP score compared with the control, as in the siRNA against the G356D mutation. In order to test an ASP-RNAi effect depending on the difference in base at the mismatch site, the mismatch base at the 5th position was changed to U, G, and C (in the diagram, the resulting siRNAs were designated as siR206H_8s(A5U)19, siR206H_8s(A5G)19, and siR206H_8s(A5C)19, respectively). As a result, no large difference was observed among the bases, demonstrating that any base forming a mismatch may be used. Most of the siRNAs used here had 8 nucleotides upstream from the standard mutation point. As is evident from these results, the siRNA against G356D having such 8 nucleotides produced substantially the same results as in the siRNAs containing 9 or 10 nucleotides upstream therefrom. In addition, as a result of testing siR206H_7s(A5U)18 and siR206H_7s(A5U)19 having 7 bases (nucleotides) upstream from the standard mutation point, a high discrimination ratio and ASP score were also obtained.

The results described above demonstrated that the structural features of the RNAi molecule suitable for ASP-RNAi induction were that the 5' end of the sense strand was located at any of the 7th to 10th positions upstream (5' side) from the standard mutation point and a mismatch base was introduced at any of the 3rd to 8th positions downstream from the standard mutation point.

Example 2

Activation of Intracellular BMP Signaling Pathway Using ALK2-siRNA

ALK2-siRNA that exhibited an effective expression suppressive effect on mutant ALK2 (R206H or G356D) in Example 1 was selected and tested for whether or not it exhibited a similar effect on full-length mutant ALK2 at the protein level.

(1) Cell Culture

Mouse myoblast cell line C2C12 cells were cultured using a DMEM culture solution (Wako Pure Chemical Industries, Ltd.) containing 15% fetal bovine serum (FBS; Invitrogen Corp.) and antibiotics (100 units/mL penicillin and 100 µg/mL streptomycin; Wako Pure Chemical Industries, Ltd.).

(2) Transfection

On the day before gene transfer, the cells were dispersed by trypsin digestion. The cell dispersion was then adjusted to a cell density of $1 \times 10^5$ cells/cm$^2$, inoculated to a 24-well culture plate, and cultured in an antibiotic-free DMEM culture solution. 24 hours later, the cells in each well were cotransfected with 200 ng/well of two types of plasmids: (1) a V5-tagged full-length normal ALK2 gene plasmid (V5-WT-ALK2) and (2) an R206H mutant ALK2 gene expression plasmid (V5-R206H-ALK2) or a G356D mutant ALK2 gene expression plasmid (V5-G356D-ALK2) (causative of disease), and (3) 20 nM/well of siR206H_8s(A5C)19 or siG356D_9s(U3A)19 that induced ALK2-RNAi evaluated by the assay described above. The basic method followed the method descried in the paragraph "(4) Transfection and reporter assay" in Example 1. A similar experiment was conducted using the comparative control siControl (Qiagen) (final concentration: 20 nM) that did not induce RNAi. 48 hours after the nucleic acid transfer, cell extracts were prepared using a cell lysis solution (50 mM Tris-HCl, pH 7.5, and 0.1% Triton-X 100).

(3) Western Blotting

The protein concentration of the cell extracts thus prepared from each cell was determined using Protein Quantification kit (DOJINDO LABORATORIES) according to the protocol included therein. 10 µg of each sample was mixed with 4× sample buffer (0.25 M Tris-HCl, 40% glycerol, 8% SDS, 0.04% bromophenol blue, and 8% β-mercaptoethanol) and heat-treated at 100° C. for 5 minutes. The heat-treated protein sample was separated on 10% SDS-polyacrylamide gel by electrophoresis (CV 50 V, 30 min.; subsequently, CV 75 V, 2 hr.) and then electroblotted (CC 100 mA, 45 min.) onto a PVDF membrane (Immobilon P; Millipore Corp.). The membrane was dipped in a blocking solution (5% Difco skim milk (BD, Becton, Dickinson and Company), 1×PBS (Wako Pure Chemical Industries, Ltd.), and 0.1% Tween-20) at room temperature for 1 hour, washed with 1×PBS (Wako Pure Chemical Industries, Ltd.), and then reacted (4° C., 16 hr.) with mouse monoclonal anti-V5 antibodies (Invitrogen Corp.) as primary antibodies diluted 5,000-fold with PBS. Next, the membrane was washed several times with PBS-T (1×PBS (Wako Pure Chemical Industries, Ltd.) and 0.1% Tween-20) at room temperature and reacted (room temperature, 1 hr.) with peroxidase-conjugated anti-mouse IgG antibodies (Sigma-Aldrich Corp.) as secondary antibodies (1:5,000 dilution). After washing several times with PBS-T at room temperature, antibody-reacted proteins were detected using Immobilon Western Chemilum HRP Substrate (Millipore Corp.) according to the protocol included therein. After the protein band detection, the antibodies on the membrane were removed using Re-Blot Plus Strong Solution (Millipore Corp.), and the membrane was washed with PBS-T. Blocking treatment was performed in the same way as above, and the membrane was then reacted (4° C., 16 hr.) with mouse monoclonal anti-α tubulin antibodies (Sigma-Aldrich Corp.) as primary antibodies (1:10,000 dilution). Subsequent operation was performed in the same way as above. The images of proteins detected as bands on an exposed film (FIGS. 5A and 5C) were captured into a scanner and then converted to numbers using Scion Image (Scion Corp.) for quantification (FIGS. 5B and 5D).

(4) Results

Figure 5:
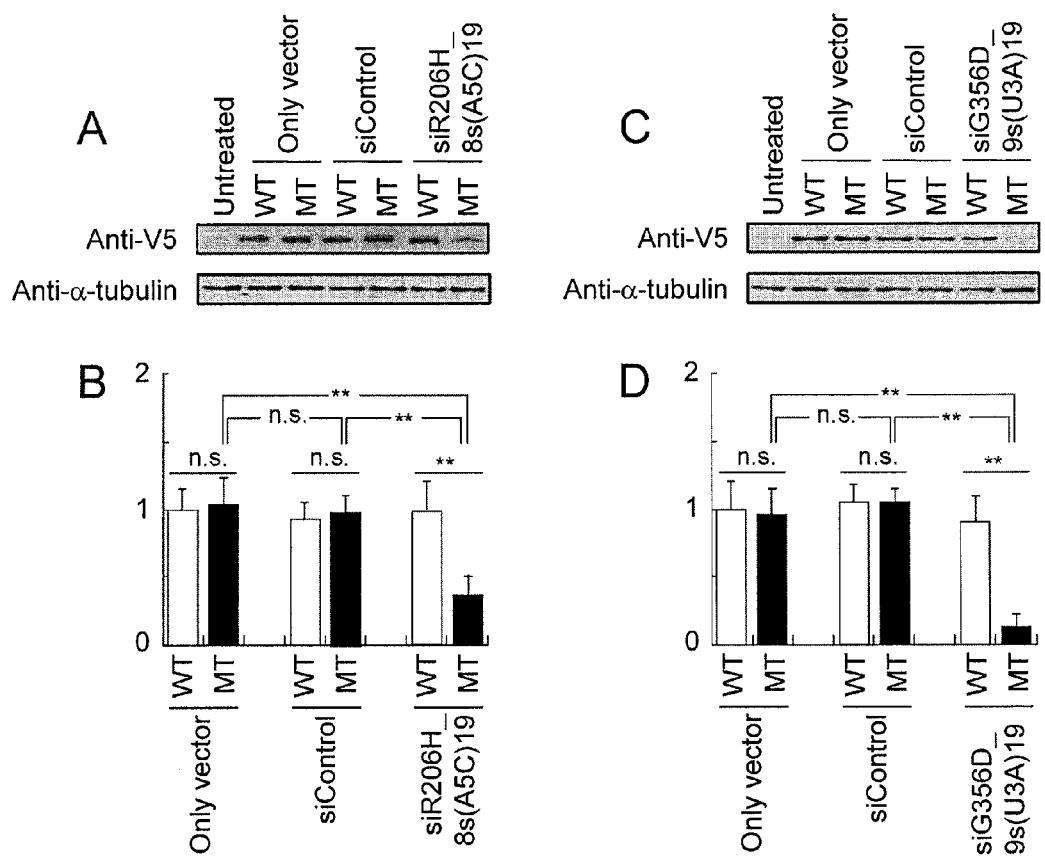
FIG. 5 shows the ASP-RNAi effects of ALK2-R206H-siRNA and ALK2-G356D-siRNA on full-length wild-type ALK2 and mutant ALK2 at the protein level.

The results are shown in FIG. 5. In FIGS. 5A and 5C, the "untreated" samples represent proteins extracted from untransfected C2C12 cells. As shown in this diagram, siR206H_8s(A5C)19 or siG356D_9s(U3A)19 remarkably and specifically exhibited a suppressive effect only on the expression of each mutant ALK2(MT)ALK2-R206H or ALK2-G356D without suppressing the expression of normal ALK2 (WT), demonstrating that preferable ASP-RNAi induction was achieved at the protein level.

Example 3

Test on ASP-RNAi Effect of siRNA Against Huntingtin Gene

For the allele-specific gene silencing of mutant huntingtin (HTT) gene, the causative gene of Huntington's disease (HD), various siRNAs (HTT-siRNAs) targeting single-nucleotide polymorphisms (SNPs) present within the transcribed sequence of the gene were designed and tested for their ASP-RNAi effects on two types of alleles.

(1) Design and preparation of HTT-siRNA

Each HD patient has, as a mutation, abnormal expansion of a CAG repeat sequence present within exon 1 of human HTT gene (Accession No. NM_002111.6). Since this CAG repeat sequence is also present in the normal allele, RNAi directly targeting the CAG repeat sequence suppresses not only the expression of the target allele but the expression of the normal allele. Thus, an SNP site with allelic heterozygosity within the transcribed sequence of the causative gene of the disease was used as a standard mutation point, and various HTT-siRNAs were designed using the design method of the present invention and evaluated for their RNAi effects. Table 4 shows the nucleotide sequences of the sense and antisense strands of HTT-siRNAs designed against two SNP sites (rs363099 and rs362331) (these siRNAs were designated as siRs099 and siRs331, respectively). In this regard, nucleotide sequences are shown in each table except for their 3'-terminal UU overhang sequences in sense and antisense strands for the sake of convenience.

TABLE 4

| siRNA name | sense/<br>anti-<br>sense | Nucleotide sequence<br>(5' → 3') | SEQ<br>ID<br>NO: |
|---|---|---|---|
| siRs331_8s19 | ss | CCCUCAUCCACUGUGUGCA | 53 |
| | as | UGCACUCAGUGGAUGAGGG | 54 |
| siRs331_8s(G4C)19 | ss | CCCUCAUCCACUCUGUGCA | 55 |
| | as | UGCACAGAGUGGAUGAGGG | 56 |
| siRs331_8s(U5A)19 | ss | CCCUCAUCCACUGAGUGCA | 57 |
| | as | UGCACUCAGUGGAUGAGGG | 58 |
| siRs331_8s(G6C)19 | ss | CCCUCAUCCACUGUCUGCA | 59 |
| | as | UGCAGACAGUGGAUGAGGG | 60 |
| siRs331_8s(U7A)19 | ss | CCCUCAUCCACUGUGAGCA | 61 |
| | as | UGCUCACAGUGGAUGAGGG | 62 |
| siRs331_8s(G8C)19 | ss | CCCUCAUCCACUGUGUCCA | 63 |
| | as | UGGACACAGUGGAUGAGGG | 64 |
| siRs099_8s19 | ss | GGGUUUCUCCGCUCAGCCU | 65 |
| | as | AGGCUGAGCGGAGAAACCC | 66 |
| siRs099_8s(U4A)19 | ss | GGGUUUCUCCGCACAGCCU | 67 |
| | as | AGGCUGUGCGGAGAAACCC | 68 |
| siRs099_8s(G5C)19 | ss | GGGUUUCUCCGCUGAGCCU | 69 |
| | as | AGGCUGAGCGGAGAAACCC | 70 |

The chemical synthesis and annealing treatment of each siRNA were performed in the same way as in Example 1 on the basis of the nucleotide sequences of Table 3.

(2) Construction of Reporter Allele Expression Plasmid

In order to evaluate the RNAi effects of the HTT-siRNAs prepared in the preceding paragraph (1) and select suitable HTT-siRNAs, an SNP with high allelic heterozygosity and its neighboring sequences were inserted to the 3' UTR of each luciferase gene similarly to the method described in "Example 1(2)" to construct reporter allele expression plasmids.

Specifically, 41-base sense and antisense strands of each oligo DNA containing any of both SNP allele bases of each SNP site (Accession No. rs363099 or rs362331) within the transcribed sequence of the HTT gene as a standard mutation point site were chemically synthesized (the synthesis was entrusted to Sigma-Aldrich Corp.). Table 5 shows the specific sequence of each oligo DNA. In this table, the SNP site in each sense strand is indicated by boldface, and the linker sequences are underlined.

TABLE 5

| Sequence<br>name | sense/<br>antisense | Nucleotide sequence (5' → 3') | SEQ ID<br>NO: |
|---|---|---|---|
| rs363099(C) | ss | CTAGCATGCGTTTGGAGGGTTTCTCCGCTCAGCCTTGGATA | 71 |
| | as | GGCCTATCCAAGGCTGAGCGGAGAAACCCTCCAAACGCATG | 72 |
| rs363099(T) | ss | CTAGCATGCGTTTGGAGGGTTTCTTCGCTCAGCCTTGGATA | 73 |
| | as | GGCCTATCCAAGGCTGAGCGAAGAAACCCTCCAAACGCATG | 74 |
| rs362331(C) | ss | CTAGCATGCGCCTGCTCCCTCATCCACTGTGTGCACTTCAA | 75 |
| | as | GGCCTTGAAGTGCACACAGTGGATGAGGGAGCAGGCGCATG | 76 |
| rs362331(T) | ss | CTAGCATGCGCCTGCTCCCTCATCTACTGTGTGCACTTCAA | 77 |
| | as | GGCCTTGAAGTGCACACAGTAGATGAGGGAGCAGGCGCATG | 78 |

Next, the synthesized oligo DNA strands were subjected to annealing treatment and insertion operation into plasmids in the same was as in "Example 1(2)" to construct reporter allele expression plasmids.

(3) Cell Culture

HeLa cells (human-derived cell line) were cultured in the same way as in "Example 1(3)".

(4) Transfection and Reporter Assay

In the same way as in "Example 1(4)", the cells were inoculated and then cotransfected with the HTT-siRNAs and the reporter allele expression plasmids, and luciferase activity was determined. Then, various HTT-siRNAs designed against both bases of each SNP base were evaluated.

(5) Results

Suitable HTT-siRNAs were selected against two allelic bases at each of the above-described two SNP sites (here, both the SNP sites had C and T alleles; see Table 5) present within the transcribed sequence of the HTT gene. At the same time, both the bases at each SNP site were assigned as distinct standard mutation points, and the influence of changes in structural features such as mismatch sites was evaluated to study the general structural rule of the RNAi molecules suitable for ASP-RNAi induction.

The expression suppressive effect of each siRNA was evaluated in the same way as in Example 1 according to a discrimination ratio and an ASP score calculated on the basis of reporter luciferase activity derived from each of one HTT-SNP allele (defined as a C base allele) and the other HTT-SNP allele (defined as a T base allele). In this Example, the respective C base alleles at these two SNP sites were regarded as target alleles (i.e., mutant alleles).

Figure 6:
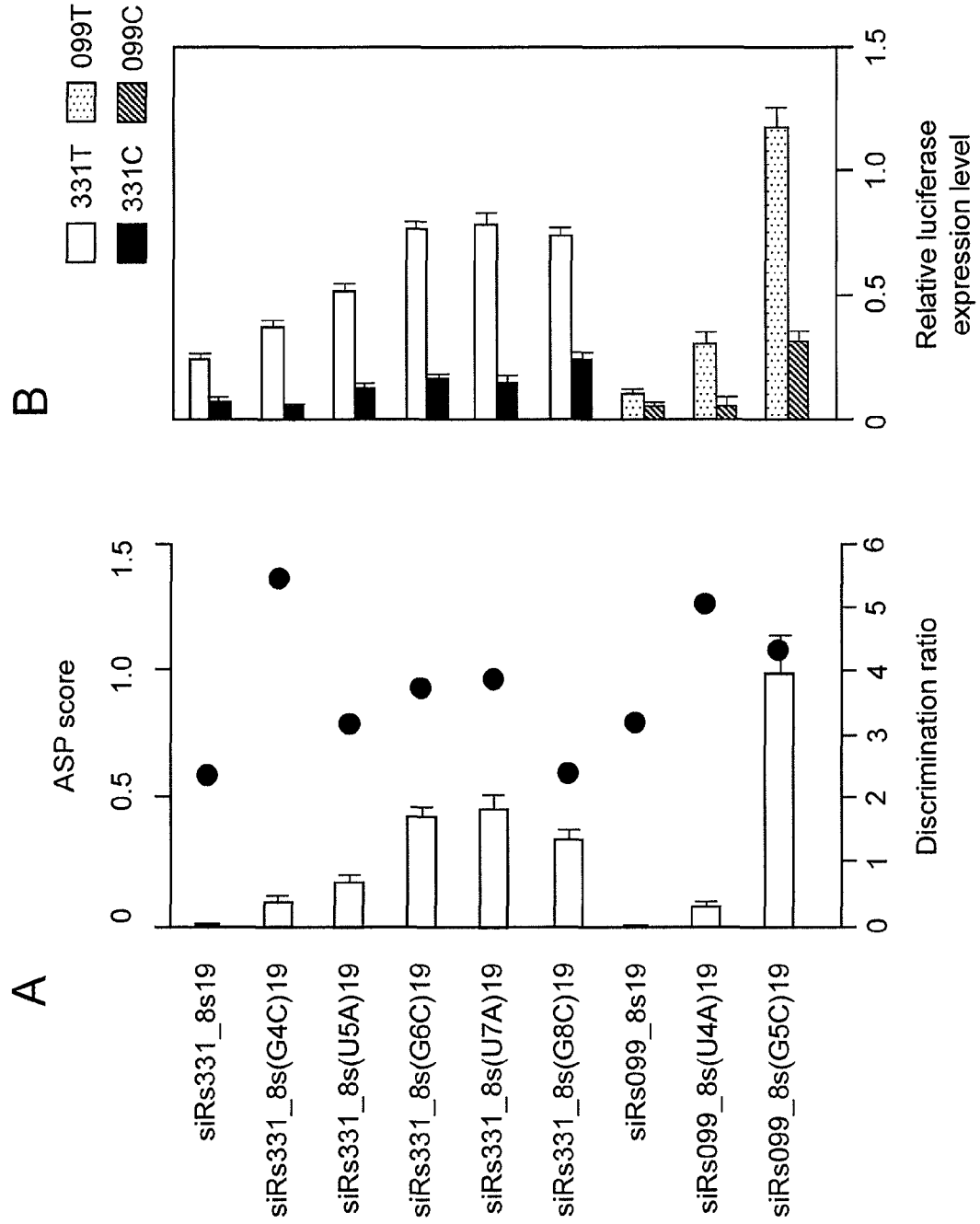
FIG. 6 shows the ASP-RNAi effect of HTT-siRNA on mutant HTT.

The results are shown in FIG. 6. FIG. 6A shows the discrimination ratio (plot) and ASP score (bar graph) of each siRNA used. FIG. 6B shows the luciferase expression levels derived from HTT with the C base allele and HTT with the T base allele.

As in Example 1, the control siRs331_8s19 targeting rs362331 was designed to consist of mismatch base-free 19 bases in full length with 8 nucleotides upstream from the standard mutation point. siRNAs in which the position of the mismatch base in the control was displaced one by one were tested for their ASP-RNAi effects. The control had a discrimination ratio of 2.89 and an ASP score of 0.04. By contrast, all the siRNAs (siRs331_8s(G4C)19 to siRs331_8s(G8C)19) containing mismatch bases at the 4th to 8th positions, respectively, downstream from the standard mutation point produced a high discrimination ratio and ASP score compared with the control. This result is consistent with the result of Example 1.

A similar test was further conducted on the control siRs099_8s19 against the other SNP site (rs363099) consisting of mismatch base-free 19 bases in full length with 8 nucleotides upstream from the standard mutation point and siRNAs (siRs099_8s(U4A)19 and siRs099_8s(G5C)19) containing mismatch bases at the 4th and 5th positions, respectively, downstream from the standard mutation point. This result also showed that the siRNA containing a mismatch at the predetermined position had a higher discrimination ratio and ASP score than those of the control.

The results described above demonstrated that the siRNA having the structural features based on the design method of the present invention was applicable to any gene and had a high ASP-RNAi effect even against an SNP mutation.

Example 4

ASP-RNAi Effect of HTT-siRNA on Endogenous Mutant Huntingtin Gene (1) Cell Culture An HD patient-derived cell line (C0221; kindly provided by Department Neurology, National Center Hospital, National Center of Neurology and Psychiatry (NCNP), Japan) was cultured at 37° C. under 5% $CO_2$ using an RPMI1640 culture solution (Wako Pure Chemical Industries, Ltd.) containing 10% fetal bovine serum (FBS; Japan Bio Serum), sodium pyruvate (110 mg/L; Wako Pure Chemical Industries, Ltd.), D-glucose (4500 mg/L; Wako Pure Chemical Industries, Ltd.), and antibiotics (100 units/mL penicillin and 100 μg/mL streptomycin; GIBCO/Life Technologies Corp.). A healthy person (without HD)-derived cell line (kindly provided by Department Neurology, National Center Hospital, National Center of Neurology and Psychiatry (NCNP), Japan) was cultured as a control in the same way as above.

(2) Transfection of HTT-siRNA by Electroporation

These two types of cells i.e., HD patient-derived cell line (C0221 lymphoblastoid cells) and healthy person-derived cell line, cultured in the preceding paragraph (1) were separately collected by centrifugation (120 G, 5 min.) and suspended at a concentration of approximately $1 \times 10^6$ cells in 100 μL of an electroporation buffer (Amaxa Cell Line Nucleofector Solution V, Amaxa) containing the HTT-siRNA (final concentration: 5 μM). These two samples for electroporation thus prepared were subjected to nucleic acid transfer by electroporation (program: U-005, gene transfer system Nucleofector, Amaxa) according to the protocol included therein. The introduced nucleic acid was a control siRNA (Qiagen) that did not induce RNAi or siRs099_8s(G5C)19.

The two C0221 cells transfected with the nucleic acid, untreated C0221 cells, and the healthy person-derived cell line were separately cultured in a 6-well culture plate using the culture solution of the paragraph (1) and collected 48 hours later.

(3) Western Blotting

Each cell collected in the preceding paragraph (2) was lysed using a cell lysis solution (20 mM Tris-HCl, pH 7.5, 150 mM NaCl, 1 mM EGTA, and 1% Triton X-100) containing 1× protease inhibitor (Roche), and the protein concentration of the cell extracts was determined using Protein Quantification kit (DOJINDO LABORATORIES) according to the protocol included therein. 20 μg of each sample was mixed with 4× sample buffer (0.25 M Tris-HCl, 40% glycerol, 8% SDS, 0.04% bromophenol blue, and 8% β-mercaptoethanol) and heat-treated at 100° C. for 5 minutes. The heat-treated protein sample was separated on modified SDS-polyacrylamide gel and a Tricine-based electrophoresis buffer (Tris/Tricine/SDS buffer, Bio-Rad Laboratories, Inc.) by electrophoresis (CV 50 V, 2 hr.; subsequently, CV 100 V, approximately 30 hr.) and then electroblotted (CC 100 mA, 1 hr.) onto a PVDF membrane (Immobilon P; Millipore Corp.). The specific composition of the modified SDS-polyacrylamide gel was as follows: separation gel: 5 to 20% acrylamide concentrations of step gradient gel (acrylamide/N,N'-methylenebisacrylamide=30:0.135), and concentration gel: 4% acrylamide gel (acrylamide/N,N'-methylenebisacrylamide=37.5:1)). The membrane after the electroblotting was dipped in a blocking solution (5% Difco skim milk (BD, Becton, Dickinson and Company), 1×PBS (Wako Pure Chemical Industries, Ltd.), and 0.1% Tween-20) at room temperature for 1 hour, washed with 1×PBS (Wako Pure Chemical Industries, Ltd.), and then reacted (4° C., 16 hr.) with mouse monoclonal anti-huntingtin antibodies (clone 1HU-4C8; Millipore Corp.) as primary antibodies diluted 3,000-fold with PBS. Next, the membrane was washed several times with PBS-T (1×PBS (Wako Pure Chemical Industries, Ltd.) and 0.1% Tween-20) at room temperature and reacted (room temperature, 1 hr.) with peroxidase-conjugated anti-mouse IgG antibodies (Sigma-Aldrich Corp.) as secondary antibodies (1:5,000 dilution). After washing several times with PBS-T at room temperature, antibody-reacted proteins were detected using Immobilon Western Chemilum HRP Substrate (Millipore Corp.) according to the protocol included therein. After the protein band detection, the antibodies on the membrane were removed using Re-Blot Plus Strong Solution (Millipore Corp.), and the membrane was washed with PBS-T. Blocking treatment was performed in the same way as above, and the membrane was then reacted (4° C., 16 hr.) with mouse monoclonal anti-αtubulin antibodies (Sigma-Aldrich Corp.) as primary antibodies (1:10,000 dilution). Subsequent operation was performed in the same way as in Example 2.

(4) Results

Figure 7:
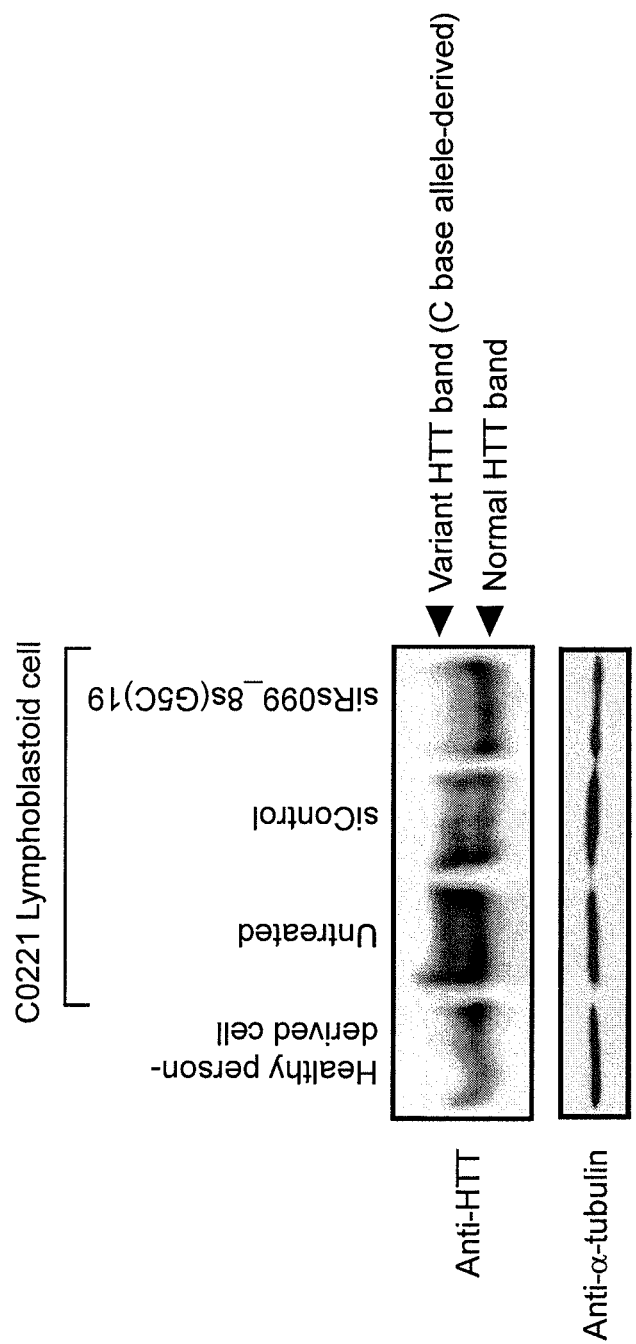
FIG. 7 shows the ASP-RNAi effect of HTT-siRNA on full-length wild-type HTT and mutant HTT at the protein level.

The results are shown in FIG. 7. Only the band of the normal HTT protein was observed in the healthy person, whereas both the band of the normal HTT protein and the band of the mutant HTT protein (C base allele-derived) were observed in the HD patient. The band of the target C base allele-derived HTT protein disappeared in the sample of this HD patient-derived cell treated with siRs099_8s(G5C)19 prepared by the design method of the present invention. This result demonstrated that siRs099_8s(G5C)19 confirmed to have an ASP-RNAi effect in Example 3 had an ASP-RNAi effect even at the full-length protein level. The results described above also demonstrated that, against endogenous mutant HTT genes differing in SNP type, the introduction of HTT-siRNA corresponding to the SNP type was able to induce preferable ASP-RNAi and specifically suppress only the expression of the mutant HTT protein causative of the disease while leaving the normal HTT protein intact.

Example 5

Test on ASP-RNAi Effect of siRNA Against EGFR Gene

An siRNA (EGFR-siRNA) specifically suppressing the expression of mutant epidermal growth factor receptor (EGFR) gene, the causative gene of non-small cell lung cancer (NSCLC), known as a postnatally occurring dominant mutant allele was designed and tested for its ASP-RNAi effect on each of a dominant allele and a wild-type allele.

The binding of a ligand such as epidermal growth factor (EGF) to the extracellular domain of EGFR activates tyrosine kinase in the intracellular domain, which is in turn autophosphorylated to direct the downstream intracellular signaling pathways. Non-small cell lung cancer is thought to be developed by a point mutation or deletion at a particular base in the EGFR gene resulting in a gain-of-function mutation (Paez G. J. et al., Science, 2004, 304; 1497-1500). Accordingly, the EGFR-siRNA of the present invention can serve as an effective therapeutic agent for non-small cell lung cancer provided that it can specifically suppress only the expression of the mutated EGFR gene.

(1) Design and Preparation of Egfr-siRNA

Each non-small cell lung cancer patient has a point mutation that substitutes the 2369th base C (counted from A in the start codon as the first position; the same holds true for the description below) in human EGFR gene (Accession No. NM_005228) by T (T790M amino acid mutation: tryptophan at the 790th position counted from initiating methionine is substituted by methionine). Thus, three EGFR-siRNAs were designed with this point mutation assigned as a standard mutation point according to the method for designing the RNAi molecule described in the first aspect. Table 6 shows the nucleotide sequences of sense and antisense strands of the designed siRNAs. As in Example 1, siT790M_8s18 consisted of mismatch base-free 18 bases in full length with 8 nucleotides upstream from the standard mutation point. siT790M_8s(G4C)18 and siT790M8s(U6A)18 were EGFR-siRNAs containing mismatch bases at the 4th and 6th positions, respectively, downstream from the standard point of siT790M_8s18. In this regard, nucleotide sequences are shown in each table except for their 3'-terminal UU overhang sequences in sense and antisense strands for the sake of convenience.

TABLE 6

| siRNA name | sense/anti-sense | Nucleotide sequence (5' → 3') | SEQ ID NO: |
|---|---|---|---|
| siT790M_8s18 | ss | GCUCAUCAUGCAGCUCAU | 79 |
|  | as | AUGAGCUGCAUGAUGAGC | 80 |
| siT790M_8s(G4C)18 | ss | GCUCAUCAUGCACCUCAU | 81 |
|  | as | AUGAGCUGCAUGAUGAGC | 82 |
| siT790M_8s(U6A)18 | ss | GCUCAUCAUGCAGCACAU | 83 |
|  | as | AUGUGCUGCAUGAUGAGC | 84 |

The chemical synthesis and annealing treatment of each siRNA were performed in the same way as in Example 1 on the basis of the nucleotide sequences of Table 6.

(2) Construction of Reporter Allele Expression Plasmid

In order to evaluate the RNAi effects of the EGFR-siRNAs prepared in the preceding paragraph (1) and select suitable EGFR-siRNAs, reporter allele expression plasmids were constructed for the dominant mutant EGFR gene and the normal EGFR gene similarly to the method described in "Example 1(2)".

Specifically, 35-base oligo DNA sense and antisense strands each containing the dominant point mutation site at the 2369th position of the EGFR gene responsible for non-small cell lung cancer were chemically synthesized (the synthesis was entrusted to Sigma-Aldrich Corp.). An oligo DNA against the normal allele having no dominant point mutation site was also synthesized in the same way as above. Their respective specific nucleotide sequences are shown in Table 7.

TABLE 7

| Sequence name | sense/antisense | Nucleotide sequence (5' → 3') | SEQ ID NO: |
|---|---|---|---|
| T790M(MT) | ss | CTAGCATGCGTGCAGCTCATCATGCAGCTCATGCA | 85 |
|  | as | GGCCTGCATGAGCTGCATGATGAGCTGCACGCATG | 86 |
| T790T(WT) | ss | CTAGCATGCGTGCAGCTCATCACGCAGCTCATGCA | 87 |
|  | as | GGCCTGCATGAGCTGCGTGATGAGCTGCACGCATG | 88 |

Next, the synthesized oligo DNA strands were subjected to annealing treatment and insertion operation into plasmids in the same way as in "Example 1(2)" to construct reporter allele expression plasmids.

(3) Cell Culture

HeLa cells (human-derived cell line) were cultured in the same way as in "Example 1(3)".

(4) Transfection and Reporter Assay

In the same way as in "Example 1(4)", the cells were inoculated and then cotransfected with the EGFR-siRNAs and the reporter allele expression plasmids, and luciferase activity was determined. Then, the designed EGFR-siRNAs were evaluated.

(5) Results

Figure 8:
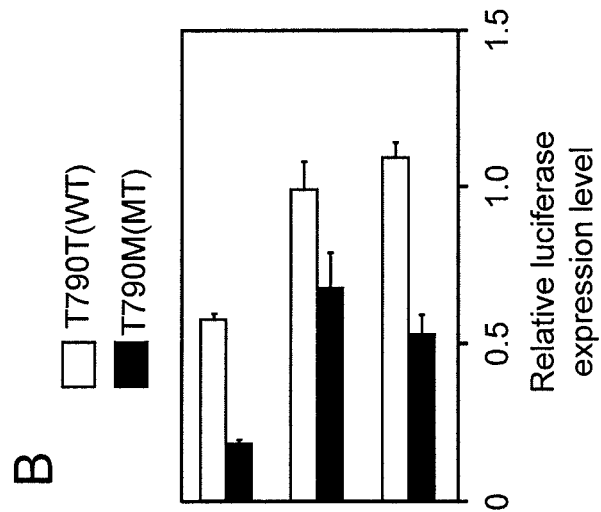
FIG. 8 shows the ASP-RNAi effect of EGFR-siRNA on mutant EGFR.
Figure 8:
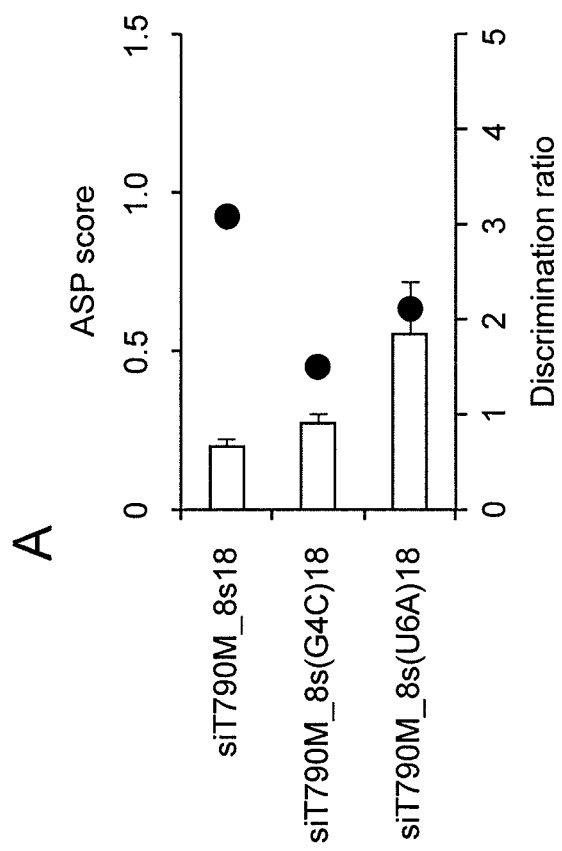

The results are shown in FIG. 8. FIG. 8A shows the discrimination ratio (plot) and ASP score (bar graph) of each siRNA used. FIG. 8B shows luciferase expression levels derived from the wild-type EGFR sequence (T790T(WT)) and the target mutant EGFR sequence (T790M(MT)).

Both siT790M_8s(G4C)18 and siT790M_8s(U6A)18 containing mismatch bases at the 4th and 6th positions, respectively, downstream from the standard mutation point produces a high discrimination ratio and ASP score compared with the control siT790M_8s18. This result is consistent with the results of Examples 1 and 3.

The results described above demonstrated that the siRNA having the structural features based on the design method of the present invention had a high ASP-RNAi effect on various genes.

All publications, patents, and patent applications cited herein are incorporated herein by reference in their entirety.

The invention claimed is:

1. An agent for suppressing expression of a dominant allele of a target gene comprising an RNAi molecule, wherein the RNAi molecule comprises an RNAi sense strand region consisting of a nucleotide sequence identical to any one 16-base to 30-base consecutive nucleotide sequence in the sense strand of the dominant allele comprising at least one dominant point mutation and an RNAi antisense strand region consisting of a nucleotide sequence complementary thereto, wherein:

any one base at the 7th to 10th positions upstream from any one dominant point mutation in the RNAi sense strand region constitutes the 5'-terminal base of the sense strand of the RNAi molecule; and any one base at the 3rd to 8th positions downstream from the any one dominant point mutation is a mismatch base different from the corresponding base in the nucleotide sequence in the sense strand of the dominant allele, wherein the dominant point mutation is involved in the onset of a non-small cell lung cancer, the target gene is epidermal growth factor receptor (EGFR) gene, and the sense and antisense strands of the RNAi molecule consist of an oligonucleotide pair shown in SEQ ID NOs; 81 and 82 or SEQ ID NOs: 83 and 84, respectively.

2. An agent for suppressing expression of a dominant allele of a target gene comprising an RNAi molecule, wherein the RNAi molecule comprises an RNAi sense strand region consisting of a nucleotide sequence identical to any one 16-base to 30-base consecutive nucleotide sequence in the sense strand of the dominant allele comprising at least one dominant point mutation and an RNAi antisense strand region consisting of a nucleotide sequence complementary thereto, wherein:

any one base at the 7th to 10th positions upstream from any one dominant point mutation in the RNAi sense strand region constitutes the 5'-terminal base of the sense strand of the RNAi molecule; and any one base at the 3rd to 8th positions downstream from the any one dominant point mutation is a mismatch base different from the corresponding base in the nucleotide sequence in the sense strand of the dominant allele, wherein the dominant point mutation is involved in the onset of fibrodysplasia ossificans progressiva, the target gene is activin-like kinase 2 (ALK2) gene, and the sense and antisense strands of the RNAi molecule are selected from the group consisting of oligonucleotide pairs shown in SEQ ID NOs: 3 and 4, SEQ ID NOs: 5 and 6, SEQ ID NOs: 7 and 8, SEQ ID NOs: 9 and 10, SEQ ID NOs: 11 and 12, SEQ ID NOs: 13 and 14, SEQ ID NOs: 19 and 20, SEQ ID NOs: 21 and 22, SEQ ID NOs: 23 and 24, SEQ ID NOs: 25 and 26, SEQ ID NOs: 27 and 28, SEQ ID NOs: 29 and 30, SEQ ID NOs: 35 and 36, SEQ ID NOs: 37 and 38, SEQ ID NOs: 39 and 40, SEQ ID NOs: 41 and 42, SEQ ID NOs: 43 and 44, and SEQ ID NOs: 91 and 92, respectively.

3. An agent for suppressing expression of a dominant allele of a target gene comprising an RNAi molecule, wherein the RNAi molecule comprises an RNAi sense strand region consisting of a nucleotide sequence identical to any one 16-base to 30-base consecutive nucleotide sequence in the sense strand of the dominant allele comprising at least one dominant point mutation and an RNAi antisense strand region consisting of a nucleotide sequence complementary thereto, wherein:

any one base at the 7th to 10th positions upstream from any one dominant point mutation in the RNAi sense strand region constitutes the 5'-terminal base of the sense strand of the RNAi molecule; and any one base at the 3rd to 8th positions downstream from the any one dominant point mutation is a mismatch base different from the corresponding base in the nucleotide sequence in the sense strand of the dominant allele, wherein the dominant point mutation is involved in the onset of Huntington's disease, the target gene is huntingtin gene, and the sense and antisense strands of the RNAi molecule are selected from the group consisting of oligonucleotide pairs shown in SEQ ID NOs: 55 and 56, SEQ ID NOs: 57 and 58, SEQ ID NOs: 59 and 60, SEQ ID NOs: 61 and 62, SEQ ID NOs: 63 and 64, SEQ ID NOs: 67 and 68, and SEQ ID NOs: 69 and 70, respectively.

4. A pharmaceutical composition comprising the suppressing agent according to claim 1 as an active ingredient.

5. The pharmaceutical composition according to claim 4, further comprising a pharmaceutically acceptable carrier.

6. A pharmaceutical composition comprising the suppressing agent according to claim 2 as an active ingredient.

7. The pharmaceutical composition according to claim 6, further comprising a pharmaceutically acceptable carrier.

8. A pharmaceutical composition comprising the suppressing agent according to claim 3 as an active ingredient.

9. The pharmaceutical composition according to claim 8, further comprising a pharmaceutically acceptable carrier.

* * * * *